United States Patent
Utsunomiya et al.

(10) Patent No.: US 10,398,395 B2
(45) Date of Patent: Sep. 3, 2019

(54) MEDICAL IMAGE DIAGNOSTIC APPARATUS

(71) Applicant: Toshiba Medical Systems Corporation, Otawara-shi (JP)

(72) Inventors: Kazuki Utsunomiya, Nasushiobara (JP); Hiroshi Kurosawa, Nasushiobara (JP); Kousuke Sakaue, Nasushiobara (JP); Yusuke Kano, Nasushiobara (JP); Yoshiyasu Hayashi, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 0 days.

(21) Appl. No.: 15/098,756

(22) Filed: Apr. 14, 2016

(65) Prior Publication Data

US 2016/0307307 A1    Oct. 20, 2016

(30) Foreign Application Priority Data

Apr. 14, 2015   (JP) .................................. 2015-082885

(51) Int. Cl.
| | |
|---|---|
| *G06K 9/00* | (2006.01) |
| *A61B 6/00* | (2006.01) |
| *G06T 15/08* | (2011.01) |

(52) U.S. Cl.
CPC ............ *A61B 6/4441* (2013.01); *A61B 6/465* (2013.01); *G06T 15/08* (2013.01); *A61B 6/504* (2013.01); *G06T 2210/41* (2013.01)

(58) Field of Classification Search
CPC . G06T 2207/10116; G06T 2207/20224; G06T 2207/30048; G06T 2207/30101;
(Continued)

(56) References Cited

U.S. PATENT DOCUMENTS 5,371,778 A * 12/1994 Yanof ................. G06F 3/04845
                                                              128/922
6,480,732 B1 * 11/2002 Tanaka ................. A61B 8/5238
                                                              128/922
(Continued)

FOREIGN PATENT DOCUMENTS

| JP | 11-283052 | 10/1999 |
|---|---|---|
| JP | 2006-340939 A | 12/2006 |

(Continued)

OTHER PUBLICATIONS

Office Action dated Jul. 9, 2019, in Japanese Patent Application No. 2016-003648.

*Primary Examiner* — Bhavesh M Mehta
*Assistant Examiner* — Ian L Lemieux
(74) *Attorney, Agent, or Firm* — Oblon, McClelland, Maier & Neustadt, L.L.P.

(57) ABSTRACT

A medical image diagnostic apparatus includes storage circuitry and processing circuitry. The storage circuitry is configured to store three-dimensional medical image data that is obtained by imaging a subject. The processing circuitry is configured to set a region of attention in each of medical images of the three-dimensional medical image data corresponding to at least two directions. The processing circuitry is configured to calculate, based on the regions of attention, a region of interest in the three-dimensional medical image data on the subject. The processing circuitry is configured to calculate, based on voxel values of the region of interest, a parameter value relating to image processing on a medical image that is generated from the three-dimensional medical image data. The processing circuitry is configured to generate a display image by performing rendering processing on the basis of the three-dimensional medical image data and the parameter value.

12 Claims, 20 Drawing Sheets

(58) Field of Classification Search
CPC ....... G06T 15/08; G06T 2215/16; G06T 5/50; A61B 6/504; A61B 8/5238
See application file for complete search history.

(56) References Cited

U.S. PATENT DOCUMENTS

| | | | | |
|---|---|---|---|---|
| 6,658,080 | B1* | 12/2003 | Poole | A61B 5/7445 378/4 |
| 8,311,279 | B2* | 11/2012 | Quarfordt | G06K 9/0061 382/100 |
| 8,442,282 | B2 | 5/2013 | Sugiyama et al. | |
| 8,467,856 | B2* | 6/2013 | Renisch | A61B 6/5217 382/130 |
| 9,092,902 | B2* | 7/2015 | Lobregt | G06T 15/08 |
| 9,830,718 | B2* | 11/2017 | Hirai | G06T 11/008 |
| 2006/0262969 | A1* | 11/2006 | Matsumoto | G06K 9/34 382/131 |
| 2009/0135175 | A1* | 5/2009 | Lobregt | G06T 15/08 345/419 |
| 2010/0324422 | A1* | 12/2010 | Wanda | A61B 5/055 600/443 |
| 2011/0054295 | A1* | 3/2011 | Masumoto | A61B 5/055 600/407 |
| 2011/0176711 | A1* | 7/2011 | Bocirnea | G06F 17/3028 382/128 |
| 2013/0137966 | A1* | 5/2013 | Nakahara | A61B 5/055 600/411 |
| 2014/0098092 | A1* | 4/2014 | Isokawa | G06T 15/08 345/419 |

FOREIGN PATENT DOCUMENTS

| | | |
|---|---|---|
| JP | 2008-6274 | 1/2008 |
| JP | 2012-100955 | 5/2012 |
| JP | 2012-247905 | 12/2012 |
| JP | 2013-111359 A | 6/2013 |
| JP | 2014-138837 A | 7/2014 |
| WO | WO 2007/114470 A1 | 10/2007 |

* cited by examiner

FIG.5
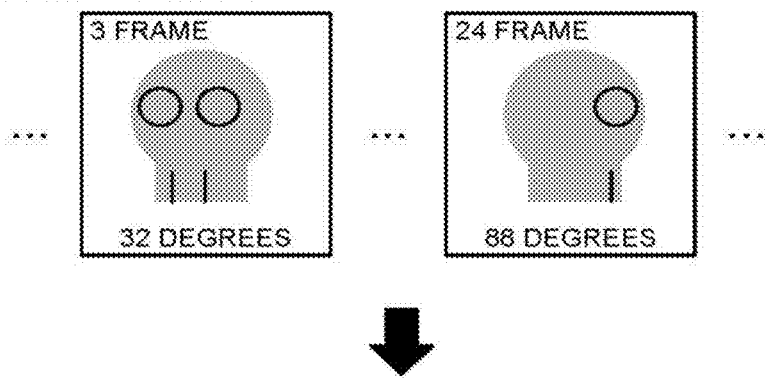
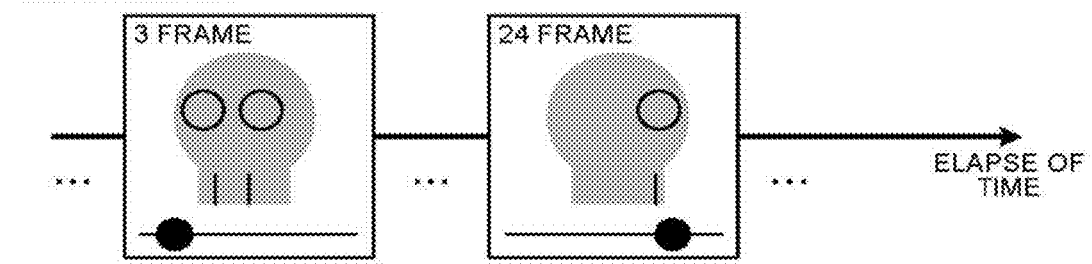

| FRAME | IMAGING ANGLE | CENTER X-COORDINATE | CENTER Y-COORDINATE | SIZE |
|---|---|---|---|---|
| ... | | | | |
| 3 | 32 | 330 | 410 | 30 |
| ... | | | | |
| 24 | 88 | 460 | 380 | 50 |
| ... | | | | |

| FRAME | <LINE-OF-SIGHT INFORMATION> | | <CENTER REGION INFORMATION> | | |
| --- | --- | --- | --- | --- | --- |
| | X-COORDINATE | Y-COORDINATE | CENTER X-COORDINATE | CENTER Y-COORDINATE | SIZE |
| 3 | 300 | 404 | 330 | 410 | 30 |
| | 315 | 418 | | | |
| | 360 | 408 | | | |
| 4 | | | | | |
| 5 | | | | | |
| ... | ... | ... | ... | ... | ... |
| 24 | 440 | 405 | 460 | 380 | 50 |
| | 480 | 355 | | | |

MEDICAL IMAGE DIAGNOSTIC APPARATUS

CROSS-REFERENCE TO RELATED APPLICATIONS

This application is based upon and claims the benefit of priority from Japanese Patent Application No. 2015-82885, filed on Apr. 14, 2015; the entire contents of which are incorporated herein by reference. The entire contents of the prior Japanese Patent Application No. 2016-3648, filed on Jan. 12, 2016, are also incorporated herein by reference.

FIELD

Embodiments described herein relate generally to a medical image diagnostic apparatus.

BACKGROUND

A conventional medical image diagnostic apparatus, such as an X-ray angiography apparatus, generates three-dimensional image data (hereinafter, also referred to as "volume data"). Based on the generated volume data, various examinations and diagnoses are carried out. For example, the volume data generated by the medical image diagnostic apparatus is converted into a two-dimensional image that reflects the three-dimensional information through volume rendering processing, and the two-dimensional image is displayed on a monitor. An observer (such as a doctor who performs manipulative operations using an X-ray angiography apparatus) performs various examinations, diagnoses, and treatments while observing the two-dimensional image displayed on the monitor.

In the above-described volume rendering processing, an arbitrary point of view with respect to a site that is a subject of examination, diagnosis, or treatment is defined and a projection surface for projecting, as a two-dimensional image, the three-dimensional volume data from the defined point of view and a line of sight from the defined point of view toward the projection surface are defined. The gradation levels of the pixels on the projection surface are then determined based on the voxel values on the light of sight from the point of view toward the projection surface. When the gradation levels on the projection surface are determined, setting an opacity for each voxel value determines the display mode of the subject site viewed from the arbitrary point of view. In other words, a setting is made about how the defined line of sight is transmitted through the subject site and on how the line of sight reflects when the projection surface is viewed from the defined point of view. The opacity is properly adjusted in order for, for example, an easy-to-see display of the site to be measured (observed).

Furthermore, as such a system applied to the X-ray angiography apparatus, a system is known where the X-ray angiography apparatus operated by an operator (such as medical technologist) who is in operation room according to an instruction from a doctor who is in examination room. The system, if it is a simple operation, can be operated by a user terminal in hand of the doctor. With the development of the user terminal (such as tablet device) can also be used for medical, the doctor has enabled more complex operations by the user terminal are disposed on hand of the doctor. With the above-described conventional technology, it may be difficult to make an easy-to-see display of a site to be observed by the doctor performs operations.

BRIEF DESCRIPTION OF THE DRAWINGS

FIG. 5 is a diagram for explaining exemplary processing performed by a display controlling unit according to the first embodiment;

DETAILED DESCRIPTION

According to an embodiment, a medical image diagnostic apparatus includes storage circuitry and processing circuitry. The storage circuitry is configured to store three-dimensional medical image data that is obtained by imaging a subject. The processing circuitry is configured to set a position of attention in each of medical images of the three-dimensional medical image data corresponding to at least two directions. The processing circuitry is configured to calculate, based on the region of attention, a region of interest in the three-dimensional medical image data on the subject. The processing circuitry is configured to calculate, based on voxel values of the region of interest, a parameter value relating to image processing on a medical image that is generated from the three-dimensional medical image data. The processing circuitry is configured to generate a display image by performing rendering processing on the basis of the three-dimensional medical image data and the parameter value.

Embodiments of the medical image diagnostic apparatus according to the present invention will be described in detail below with reference to the accompanying drawings. An X-ray angiography apparatus will be exemplified below as the medical image diagnostic apparatus disclosed herein.

First Embodiment

Figure 1A:
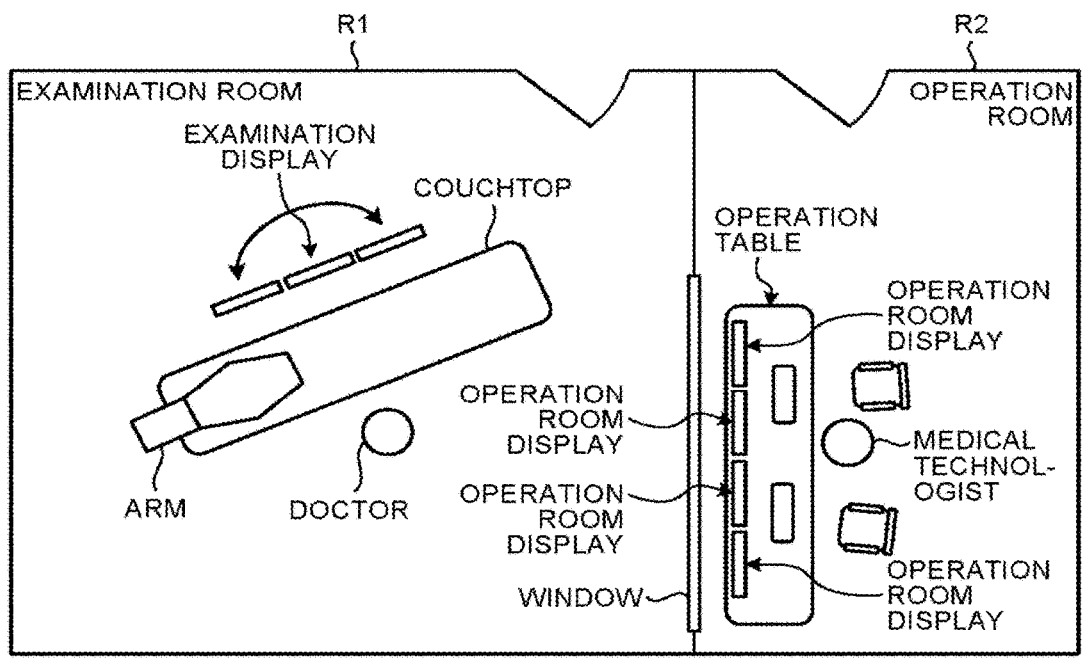
FIG. 1A is a diagram for explaining an exemplary X-ray angiography apparatus according to a first embodiment of the present invention.
Figure 1B:
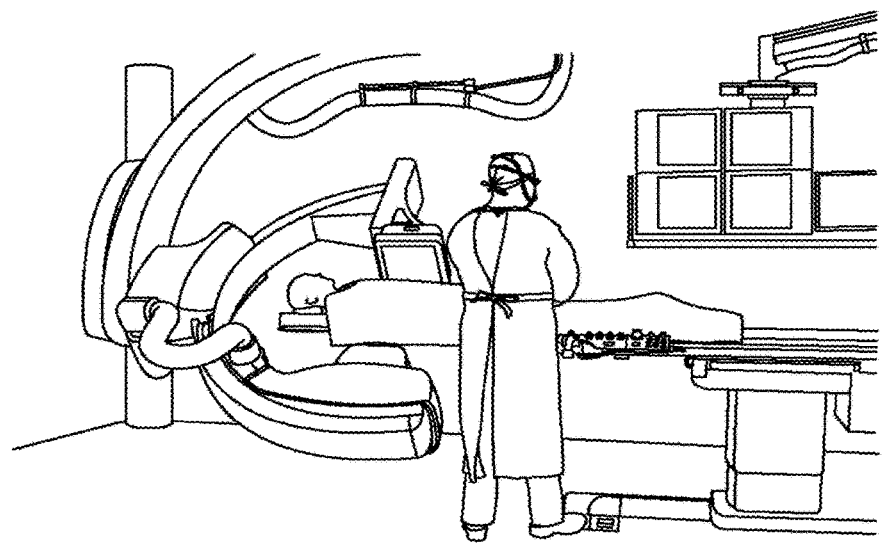
FIG. 1B is a diagram for explaining an exemplary X-ray angiography apparatus according to the first embodiment.

With reference to FIGS. 1A and 1B, the X-ray angiography apparatus according to the first embodiment will be described. FIGS. 1A and 1B are diagrams for explaining an exemplary X-ray angiography apparatus according to the first embodiment. For example, as illustrated in FIG. 1A, the apparatus main unit of the X-ray angiography apparatus, including an arm and a couchtop, is disposed in an examination room R1 in which diagnosis of and treatment for the circulatory system, such as brain or heart, is carried out. In an operation room R2 illustrated in FIG. 1A, an operation terminal that performs operations for controlling the apparatus main unit is disposed.

In the examination room R1 and the operation room R2, multiple examination room displays and multiple operation room displays are set. For example, the examination room displays are observed by a doctor who performs manipulative operations, a nurse, etc. The examination room displays are observed by an operator who performs operations to control the apparatus main unit. For example, in the examination room, the doctor who performs manipulative operations operates an operation console (such as a table side console) in the examination room to perform a cerebrovascular treatment while observing a radiographic image displayed on the examination display. Furthermore, for example, in the operation room, the medical technologist, or the like, operates the operation terminal while observing the operation room displays to make an adjustment on the image according to an instruction from the doctor.

The X-ray angiography apparatus according to the first embodiment makes it easy to make an easy-to-see display of a site to be observed. For example, in recent years, a technology of remote operations enabled by connecting the user terminal to the operation terminal disposed in the operation room R2 has become applied to X-ray angiography apparatuses like that illustrated in FIG. 1A. For example, "Splashtop touchpad" that is an application that allows a touch operation device, such as a tablet device, to access an operation terminal by WiFi (trademark) to remotely control the operation terminal, etc., have become started to be used.

According to the technology, for example, the touch operation device and the operation terminal are connected by wireless communications, and the operation terminal wirelessly receives an operation accepted by the touch operation device so that the operation terminal is remotely operated. For example, the medical technologist in the examination room R1 operates a pointer displayed on the examination room display by using the touch panel on the touch operation device as a touch pad, thereby performing an input operation on a GUI that is displayed on the examination room display.

Figure 2:
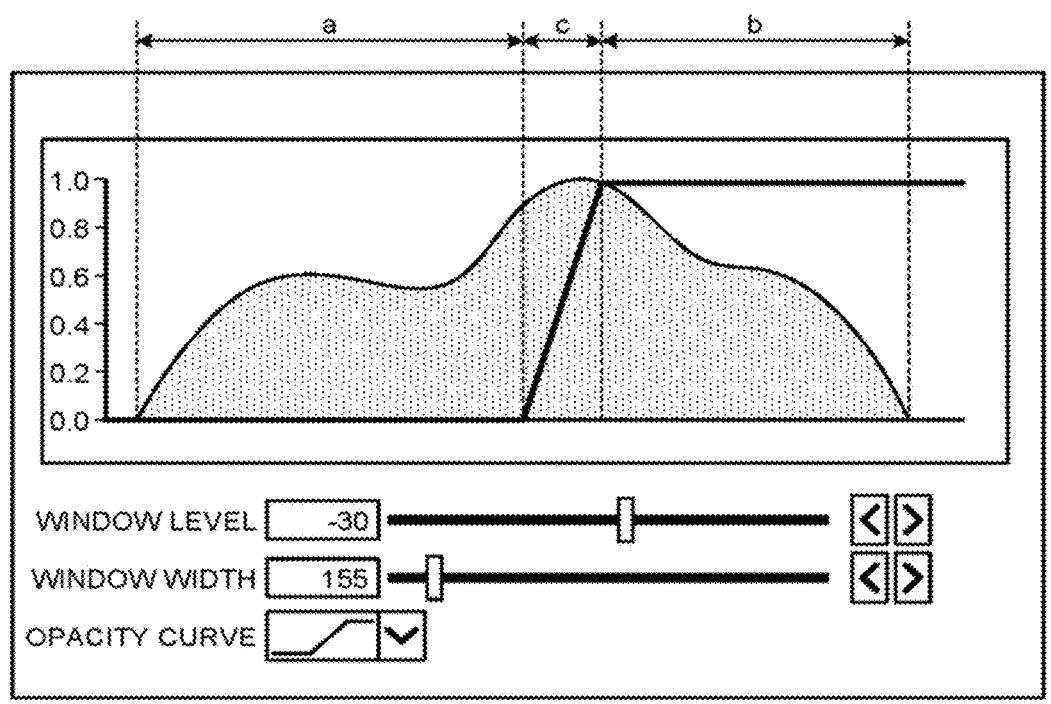
FIG. 2 is a diagram for explaining an exemplary opacity setting according to a conventional technology.

In such a system, however, it may be difficult to make an easy-to-see display of a site to be observed. For example, according to the conventional technology, to make an opacity setting as descried above, the medical technologist in the operation room inputs numeric values in text boxes, operates scale bars, and performs operations of dragging and dropping points and lines on a voxel-value histogram by using a mouse and a keyboard. FIG. 2 is a diagram for explaining an exemplary opacity setting according to the conventional technology. FIG. 2 illustrates an example where an opacity curve for making an opacity setting is set in the voxel-value histogram. In other words, according to FIG. 2, an area for which the opacity is varied and how the opacity is varied are set by using the histogram where the horizontal axis represents the voxel value.

For example, as illustrated in FIG. 2, an opacity curve that sets the opacity ratio is set in the histogram where the horizontal axis represents the voxel value. Here, "1.0" on the vertical axis represents the opacity of "100%" and "0.0" on the horizontal axis represents the opacity of "0%". In other words, with the setting illustrated in FIG. 2, the site corresponding to the voxel values of an area "a" that is the area having the opacity of "0%" is not seen at all on the image, and the site corresponding to the voxel values of an area "b" that is the area having the opacity of "100%" are clearly seen on the image. According to FIG. 2, as for an area "c" having the varying opacity ratio, the site corresponding to the voxel values in the area is reflected onto the image in accordance with the opacity curve.

There are various patterns of opacity curve in addition to the pattern shown in FIG. 2, and patterns are roughly determined for each site serving as a subject. When an opacity setting is made by using the conventional setting method illustrated in FIG. 2, for example, the operator sets an area of voxel values for which the opacity is varied by operating the slide bars for "Window Level" and "Window Width" shown in FIG. 2 or inputting numeric values in text boxes. The operator selects a pattern of opacity curve corresponding to the subject site from the pull-down menu for "Opacity Curve" shown in FIG. 2 to apply the opacity curve to the area that is set. Furthermore, the operator adjusts the inclination of the opacity curve, etc., by operating, for example, a mouse.

As described above, according to the conventional technology, the medical technologist in the operation room makes an opacity setting by performing various operations by using devices, such as a mouse and a keyboard. For example, the medical technologist in the operation room makes an opacity setting by operating the device according to an instruction from a medical technologist in the examination room. Under such a circumstance, in order for efficient manipulative operations, there has been a demand in recent year for an environment where the doctor in the examination room can directly make an opacity setting. However, it is difficult to bring, for example, a mouse and a keyboard, into an examination room in a sterile environment. Furthermore, operating a mouse and a keyboard may lower the efficiency of manipulative operations. For this reason, in recent years, there have been a progress in development of a system where a touch operation device, such as a tablet device for which development in sterilization is in progress, is brought into an examination room to allow a doctor to perform various operations through touch operations. The doctor in the examination room, however, has a difficulty in using the touch operation device to operate the slide bars or perform a numeric value input operation, which may make it difficult to make an easy-to-see display of a site to be observed. For example, the doctor wears rubber gloves having a high coefficient of friction and thus has a difficulty in performing smooth operations that can be performed with bare hands, which lowers the operability of the touch operation device. For this reason, it is difficult for the doctor to make a proper opacity setting by performing various operations so that an easy-to-see display of a site to be observed cannot be necessarily made.

Figure 3:
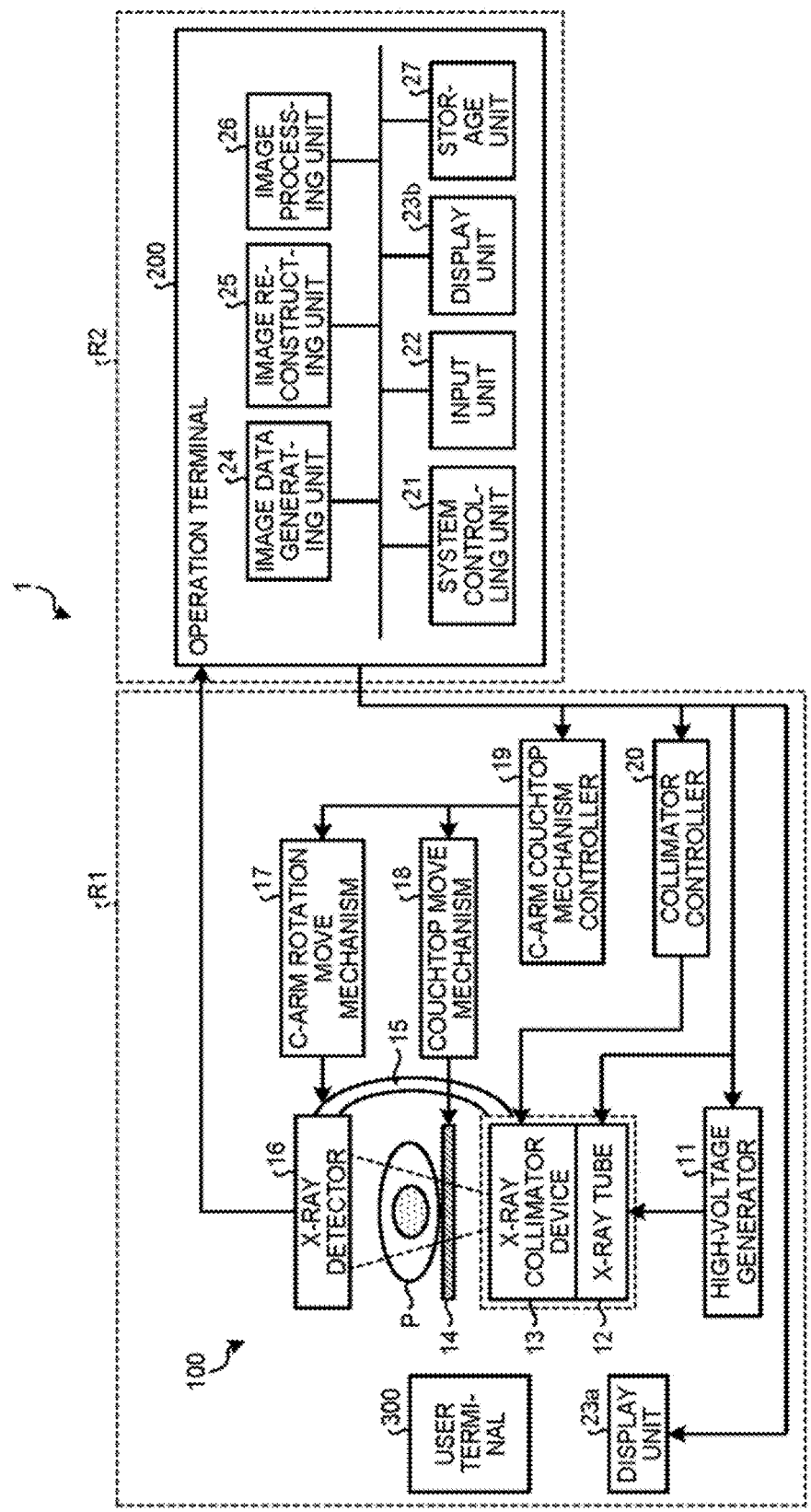
FIG. 3 is a diagram illustrating an exemplary whole configuration of an X-ray angiography apparatus according to the first embodiment.

For this reason, the X-ray angiography apparatus according the first embodiment represents candidates of opacity curve corresponding to the site to be observed by the doctor, thereby making it easy to make an easy-to-see display of the site to be observed. The details of the X-ray angiography apparatus according to the first embodiment will be described below. FIG. 3 is a diagram illustrating an exemplary whole configuration of the X-ray angiography apparatus 1 according to the first embodiment.

As shown in FIG. 3, the angiography apparatus 1 according to the first embodiment includes an apparatus main unit 100 and an operation terminal 200. As shown in FIG. 3, the apparatus main unit 100 includes a high-voltage generator 11, an X-ray tube 12, an X-ray collimator device 13, a couchtop 14, a C-arm, an X-ray detector 16, a C-arm rotation move mechanism 17, a couchtop move mechanism 18, a C-arm couchtop mechanism controller 19, a collimator controller 20, and a display unit 23a. The apparatus main unit 100 is disposed in the examination room R1. As shown in FIG. 3, the operation terminal 200 includes a system controlling unit 21, an input unit 22, a display unit 23b, an image data generating unit 24, and an image reconstructing unit 25, an image processing unit 26, and a storage unit 27. The operation terminal 200 is disposed in the operation room R2. The operation terminal 200 communicates with a user terminal 300 that is disposed in the examination room R1.

One user terminal is disposed in the examination room 1 according to FIG. 3; however, embodiments of the invention are not limited to this. For example, two or more user terminals may be disposed. Furthermore, the user terminal 300 may be disposed in each of the examination room R1 and the operation room R2. Although not shown, the X-ray angiography apparatus 1 includes an injector for injecting a contrast agent into a subject P via a catheter that is inserted into the subject P.

Under the control of the system controlling unit 21, the high-voltage generator 11 generates a high voltage and supplies the generated high voltage to the X-ray tube 12. The X-ray tube 12 generates an X-ray by using the high-voltage supplied from the high-voltage generator 11.

Under the control of the collimator controller 20, the X-ray collimator device 13 regulates the X-ray generated by the X-ray tube 12 to selectively emit the X-ray to a region of the subject P. For example, the X-ray collimator device 13 has slidable four collimator blades. Under the control of the collimator controller 20, the X-ray collimator device 13 regulates the X-ray generated by the X-ray tube 12 by sliding the collimator blades and emits the X-ray to the subject P. The X-ray tube 12 and the X-ray collimator device 13 are collectively referred also as an "X-ray tube device". The couchtop 14 is a bed on which the subject P is laid. The couchtop 14 is disposed on a couch (not shown). The apparatus main unit 100 does not include the subject P.

The X-ray detector 16 detects the X-ray having been transmitted though the subject P. For example, the X-ray detector 16 has detection elements arrayed in a matrix. Each of the detection elements converts an X-ray transmitted through the subject P into an electric signal, accumulates the electric signal, and transmits the accumulated electric signals to the image data generating unit 24.

A C-arm 15 holds the X-ray tube 12, the X-ray collimator device 13 and the X-ray detector 16. The X-ray tube 12 and the X-ray collimator device 13 are disposed by the C-arm 15 as opposed to the X-ray detector 16 with the subject in between. FIG. 1 shows the single-plane X-ray angiography apparatus 1 having the single C-arm 15. Alternatively, a bi-plane X-ray angiography apparatus having a pair of arms may be used. In this case, each of the arms holds the X-ray tube 12, the X-ray collimator device 13 and the X-ray detector 16.

The C-arm rotation move mechanism 17 is a mechanism for rotating and moving the C-arm 15. The couchtop move mechanism 18 is a mechanism for moving the couchtop 14. Under the control of the system controlling unit 21, the C-arm couchtop mechanism controller 19 controls the C-arm rotation move mechanism 17 and the couchtop move mechanism 18 to adjust rotation and move of the C-arm 15 and move of the couchtop 14. Under the control of the system controlling unit 21, the collimator controller 20 adjusts the opening of the collimator plates of the X-ray collimator device 13 to control the area to which the X-ray to be emitted to the subject P is emitted.

The image data generating unit 24 generates image data (projection data) by using electric signals converted from the X-rays by the X-ray detector 16 and stores the generated projection data in the storage unit 27. For example, the image data generating unit 24 generates the projection data by performing current-voltage conversion, analog/digital (A/D) conversion, and parallel-serial conversion on the electric signals received from the X-ray detector 16 and stores the generated projection data in the storage unit 27. The image data generating unit 24 generates an X-ray image from the generated projection data and stores the generated X-ray image in the storage unit 27.

The image reconstructing unit 25 reconstructs reconstruction data (volume data) from the projection data acquired by rotation imaging performed by the apparatus main unit 100. For example, the image reconstructing unit 25 reconstructs the volume data from the projection data stored in the storage unit 27 and stores the reconstructed volume data in the storage unit 27. The image reconstructing unit 25 also generates a three-dimensional image from the volume data and stores the three-dimensional image in the storage unit 27. For example, the image reconstructing unit 25 generates a volume rendering image or a multi Planer reconstruction (MPR) image from the volume data. The image reconstructing unit 25 stores the generated three-dimensional image in the storage unit 27. The image reconstructing unit 25 is also referred to as an "image generating unit".

The image processing unit 26 performs various types of image processing on the image data stored in the storage unit 27. For example, the image processing unit 26 generates a moving image by processing multiple X-ray images along the time sequence that are stored in the storage unit 27. The storage unit 27 stores the projection data and the X-ray image that are generated by the image data generating unit 24 and the volume data and the three-dimensional image reconstructed and generated by the image reconstructing unit 25.

The input unit 22 accepts various instructions from the operator who operates the X-ray angiography apparatus 1. For example, the input unit 22 has, for example, a mouse, a keyboard, a button, a trackball, a joystick. The input unit 22 transfers the instructions accepted from the operator to the system controlling unit 21.

The display unit 23a and the display unit 23b display a graphical user interface (GUI) for accepting instructions from the operator and the image data stored in the storage unit 27. For example, the display unit 23a is an examination room display and the display unit 23b is an operation room display. Each of the display unit 23a and the display unit 23b may include multiple displays. For example, the display unit 23a and the display unit 23b display a real-time radiographic image, a three-dimensional road map (3DRM), etc. The 3DRAM is an image obtained by superimposing the real-time radiographic image onto the projection image generated from the volume data acquired by the apparatus main unit 100.

The system controlling unit 21 controls whole operations of the X-ray angiography apparatus 1. For example, the system controlling unit 21 controls the high-voltage generator 11 according to an instruction from the operator transferred from the input unit 22 and adjusts the voltage to be supplied to the X-ray tube 12 to control the amount of X-ray emitted to the subject P and perform on/off control. Furthermore, for example, the system controlling unit 21 controls the C-arm couchtop mechanism controller 19 according to an instruction from the operator to adjust rotation and move of the C-arm 15 and move of the couchtop 14. For example, the system controlling unit 21 controls rotation imaging for acquiring projection data at a predetermined frame rate while rotating the C-arm 15. Here, while controlling rotation of the C-arm 15, the system controlling unit 21 controls the high-voltage generator 11 to sequentially or intermittently generate X-rays from the X-ray tube 12 and controls the X-ray detector 16 to detect the X-ray transmitted through the subject P. Furthermore, for example, the system controlling unit 21 controls the collimator controller 20 according to an instruction from the operator to adjust the opening of the collimator blades of the X-ray collimator device 13, thereby controlling the area to which X-rays to be emitted to the subject P are emitted.

Furthermore, according to an instruction from the operator, the system controlling unit 21 controls, for example, image data generation processing performed by the image data generating unit 24, reconstruction processing performed by the image reconstructing unit 25, image processing performed by the image processing unit 26, or analysis processing. The system controlling unit 21 performs control to display a GUI for accepting instructions from the operator and the images stored in the storage unit 27 on the displays of the display unit 23a and the display unit 23b. Furthermore, the system controlling unit 21 can control injection of a contrast agent by transmitting a signal for starting or ending injection of the contrast agent to the injector.

Figure 4:
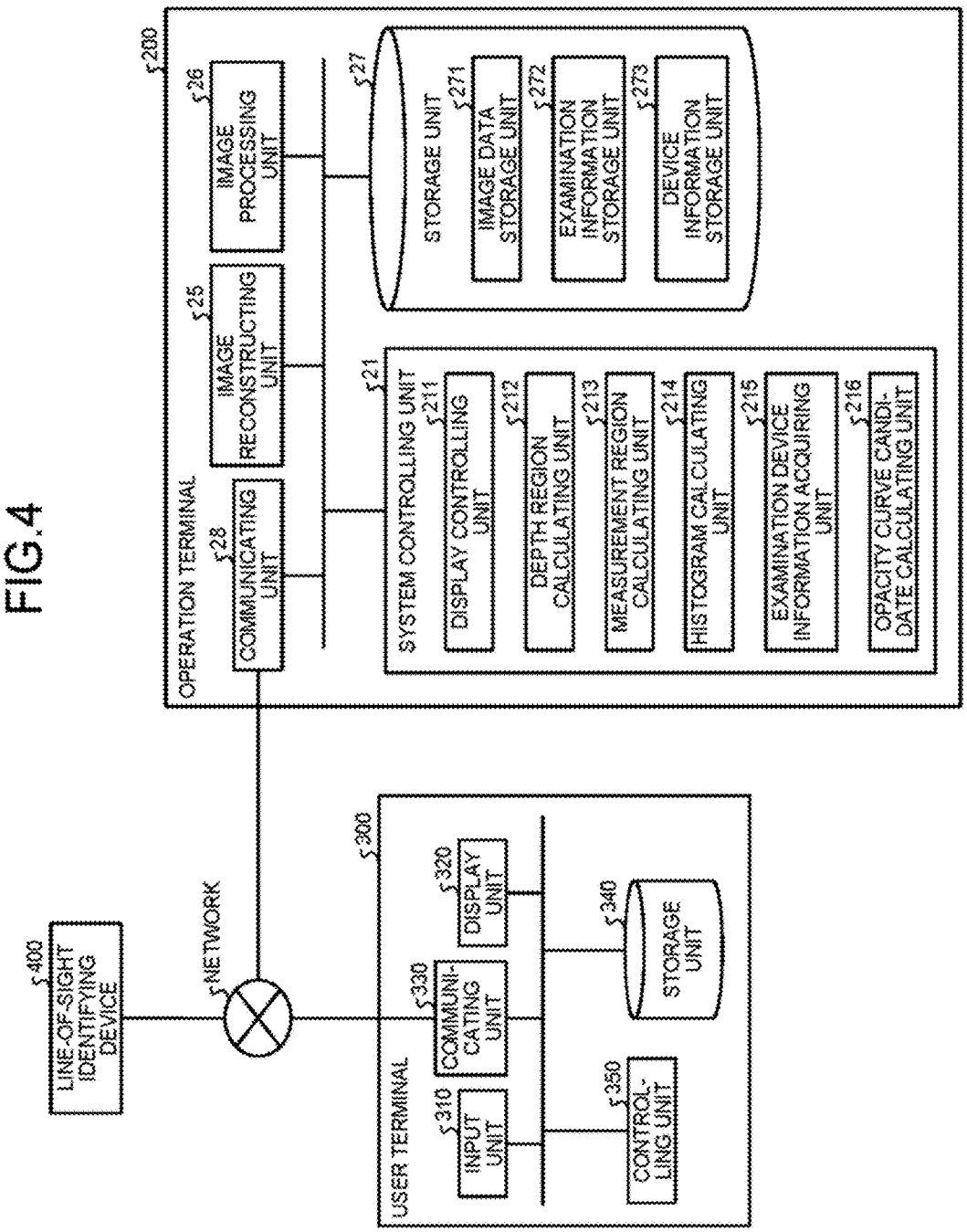
FIG. 4 is a diagram illustrating an exemplary detailed configuration of the X-ray angiography apparatus according to the first embodiment.

The whole configuration of the X-ray angiography apparatus 1 according to the first embodiment has been described. The detailed configuration of the X-ray angiography apparatus 1 according to the first embodiment will be described here with reference to FIG. 4. FIG. 4 is a diagram illustrating an exemplary detailed configuration of the X-ray angiography apparatus 1 according to the first embodiment. FIG. 4 illustrates an exemplary detailed configuration of the operation terminal 200 of the X-ray angiography apparatus 1. As shown in FIG. 4, the operation terminal 200 includes, in addition to the system controlling unit 21, the image reconstructing unit 25, the image processing unit 26, and the storage unit 27, a communicating unit 28 that is connected to the user terminal 300 and a line-of-sight identifying device 400. Although FIG. 4 does now show the input unit 22, the display unit 23b, and the image data generating unit 24, practically, the operation terminal 200 includes the input unit 22, the display unit 23b, and the image data generating unit 24 as shown in FIG. 3.

As shown in FIG. 4, the user terminal 300 includes an input unit 310, a display unit 320, a communicating unit 330, a storage unit 340, and a controlling unit 350. The user terminal 300 is a touch device, such as tablet PC. The input unit 310 is, for example, a touch panel having a rectangular platy outer shape and accepts input operations from the operator, such as a doctor or a nurse, who operates the user terminal. For example, the input unit 310 accepts various instructions by accepting a touch operation, a flick operation, a swipe operation, etc. The display unit 320 displays various types of information received from the X-ray angiography apparatus 1. For example, the display unit 320 is a display device, such as a liquid crystal panel. The display unit 320 is formed in combination with the input unit 310 and displays the GUI for the input unit 310 to accept input operations.

The communicating unit 330 is, for example, an NIC and communicates with the operation terminal 200 via the network. Specifically, the communicating unit 330 performs various communications between the communicating unit 330 and the communicating unit 28 of the operation terminal 200. The storage unit 340 is a storage device, such as a semiconductor memory device, such as a RAM or a flash memory, or a hard disk or an optical disk. The storage unit 340 stores information used by the controlling unit 350. The controlling unit 350 is, for example, an electronic circuit, such as a central processing unit (CPU) or a micro processing unit (MPU), or an integrated circuit, such as an application specific integrated circuit (ASIC) or a field programmable gate array (FPGA). The controlling unit 350 controls the whole user terminal 300.

The exemplary user terminal 300 including the input unit 310, the display unit 320, the communicating unit 330, the storage unit 340, and the controlling unit 350 has been exemplified with reference to FIG. 4. However, embodiments of the present invention are not limited to this. For example, the storage unit 340 and the controlling unit 350 may be disposed in a device, such as the operation terminal 200, different from the user terminal 300. In other words, the user terminal 300 may include the input unit 310, the display unit 320, and the communicating unit 330 and may be controlled by the controlling unit 350 that is disposed in a device, such as the operation terminal 200. In that case, the user terminal 300 receives/transmits signals from/to a device, such as the operation terminal 200, via the communicating unit 330. For example, the user terminal 300 transmits various instructions accepted by the input unit 310 to the controlling unit 350 via the communicating unit 330 or receives the result of processing performed by the controlling unit 350. The storage unit 340 and the controlling unit 350 may be newly disposed in the operation terminal 200 but, instead, the storage unit 27 may store the information stored in the storage unit 340 and the system controlling unit 21 may perform various types of processing performed by the controlling unit 350.

The line-of-sight identifying device 400 identifies the line of sight of the doctor and identifies the point of view of the doctor who observes the image displayed on, for example, the display unit 23a. Specifically, the line-of-sight identifying device 400 identifies where the point of view of the observer positions in the image displayed on the display unit 23a. For example, the line-of-sight identifying device 400 is a device having a camera for imaging the doctor. The line-of-sight identifying device 400 converts the intersection between the plane of the display surface of the display unit 23a and the line of sight into a set of coordinates of the point in an arbitrary two-dimensional coordinate system formed on the display surface and transmits the set of coordinates of the point to the operation terminal 200.

For example, the line-of-sight identifying device 400 detects the position of the eyes and the line of sight (visual direction) of the doctor from the information acquired by the camera and detects the point of view (point of gaze) of the medical technologist on the display unit 23a. For example, a two-dimensional (x-axis, y-axis) coordinate system is formed in advance on the display surface of the display unit 23a. The line-of-sight identifying device 400 detects the line of sight of the doctor from the information acquired from the camera and calculates the intersection between the detected line of sight and the display surface of the display unit 23a. With reference to the two-dimensional coordinate information on the display surface of the display unit 23a, the line-of-sight identifying device 400 calculates the set of coordinates of the intersection on the coordinate system formed by using the x-axis and the y-axis and transmits the set of coordinates to the operation terminal 200 via the communicating unit 28. For the method of detecting the line of sight, any conventional method, such as a limbus tracking method (sclera reflection method) of measuring the ocular movement by using the difference in light reflectivity between the sclera (the white of eye) and the cornea (the black of eye), may be used. The line-of-sight identifying device 400 may be a device that is set around a monitor, or may be a wearable device, such as glasses.

The communicating unit 28 is, for example, a network interface card (NIC), and communicates with each of the user terminal 300 and the line-of-sight identifying device 400 via a network. The storage unit 27 is, for example, a storage device, such as a semiconductor memory device, such as a random access memory (RAM) or a flash memory, or a storage device, such as a hard disk or an optical disk. The storage unit 27 includes an image data storage unit 271, an examination information storage unit 272, and a device information storage unit 273 and stores various types of information.

The image data storage unit 271 stores the projection data and the X-ray image that are generated by the image data generating unit 24, the reconstructed volume data and the three-dimensional image that are generated by the image reconstructing unit 25. The image data storage unit 271 is can store an X-ray image acquired by another X-ray angiography apparatus and medical images that are acquired by another modality, such as an X-ray computed tomography (CT) apparatus or an ultrasound diagnostic apparatus. The examination information storage unit 272 stores examination information, such as examination protocols containing information on the site to be examined and information on manipulative operations and patient information containing information of age, sex, height, weight, etc. The system controlling unit 21 acquires the information from a system, such as a hospital information system (HID), a radiology information system (RIS), or a picture archiving and communication system (PACS) and stores the information. The device information storage unit 273 stores information on, for example, imaging conditions including, for example, the positions of the couchtop 14 and the C-arm 15, whether there is a contrast, the imaging rate, and X-ray conditions.

The system controlling unit 21 is, for example, an electronic circuit, such as a central processing unit (CPU) or a micro processing unit (MPU), or an integrated circuit, such as an application specific integrated circuit (ASIC) or a field programmable gate array (FPGA). As described above, the system controlling unit 21 controls the whole X-ray angiography apparatus 1.

As shown in FIG. 4, the system controlling unit 21 includes a display controlling unit 211, a depth region calculating unit 212, a measurement region calculating unit 213, a histogram calculating unit 214, an examination device information acquiring unit 215, and an opacity curve candidate calculating unit 216. The system controlling unit 21 represents candidates of opacity curve corresponding to the site to be observed by the medical technologist, which makes it easy to make an easy-to-see display of the site to be observed. The processing performed by each of the units will be described below. The above-described display controlling unit 211 is also referred to as a "presentation unit" or a "candidate display processing unit". The depth region calculating unit 212 and the measurement region calculating unit 213 are also referred to as a "calculating unit". The opacity curve candidate calculating unit 216 is also referred to as a "setting value calculating unit".

The display controlling unit 211 performs control to display the radiographic image acquired by the X-ray angiography apparatus 1 and a captured image on the display units 23a and 23b and the display unit 320 of the user terminal 300. Furthermore, the display controlling unit 211 performs control to display the various types of information on the display units 23a and 23b and the display unit 320 of the user terminal 300. For example, the display controlling unit 211 performs control to display the moving image generated by the image processing unit 26 on the display unit 23a disposed in the examination room R1.

FIG. 5 is a diagram for explaining an exemplary processing performed by the display controlling unit 211 according to the first embodiment. FIG. 5 shows an example where a moving image captured while the C-arm 15 is being rotated. For example, when the system controlling unit 21 controls the apparatus main unit 100 to perform rotation imaging, multiple X-ray images (denoted with "FRAME" in FIG. 5) obtained by imaging the subject at each angle are acquired as shown in the upper stage denoted by "IMAGE ACQUISITION" in FIG. 5. The display controlling unit 211 displays a moving image by displaying the acquired multiple frames on the display unit 23a according to the time sequence while sequentially updating the frames.

Figures 6A, 6B:
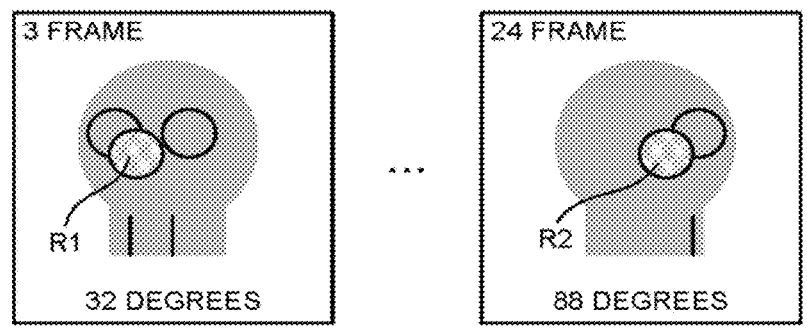
FIG. 6A is a diagram for illustrating regions of attention according to the first embodiment.
FIG. 6B is a table for illustrating regions of attention according to the first embodiment.

The doctor observes the moving image displayed on the display unit 23 and sets a region of attention (attention position). The medical technologist sets a region of attention in each of images in at least two directions. FIGS. 6A and 6B are diagrams for explaining the region of attention according to the first embodiment. FIGS. 6A and 6B show the case where a region of attention R1 and a region of attention R2 are set in the X-ray images of the third and 24th frames from among the moving image. For example, as shown in FIG. 6A, the doctor sets the region of attention R1 in the third frame and sets the region of attention R2 in the 24th frame.

As shown in FIG. 6B, the regions of attention set as described above have, for the respective frames, information of "IMAGING ANGLE", "CENTER X-COORDINATE", "CENTER Y-COORDINATE", AND "SIZE". The "IMAGING ANGLE" shown in FIG. 6B represents the angle of the C-arm 15 at which a frame where a region of attention is set is imaged. The "CENTER X-COORDINATE" shown in FIG. 6B represents the value of the x-coordinate of the center of the region of attention on the coordinate system, which is formed by the x-axis and the y-axis on the display unit 23a. The "CENTER Y-COORDINATE" shown in FIG. 6B represents the value of the y-coordinate of the center of the region of attention on the coordinate system, which is formed by the x-axis and the y-axis on the display unit 23a.

For example, "FRAME: 3, IMAGING ANGLE: 32, CENTER X-COORDINATE: 330, CENTER Y-COORDINATE: 410, and SIZE: 30" represent that the region of attention R1 of "SIZE: 30" is set at "CENTER COORDINATES (330, 410)" in "FRAME: 3" obtained at "IMAGING ANGLE: 32 DEGREES". Similarly, "FRAME: 24, IMAGING ANGLE: 88, CENTER X-COORDINATE: 460, CENTER Y-COORDINATE: 380, and SIZE: 50" represents that the region of attention R2 of "SIZE: 50" is set at "CENTER COORDINATES (460,380)" in "FRAME: 24" obtained at "IMAGING ANGLE: 88 DEGREES". The case where the regions of attention are set in the frames in two directions has been exemplified; however, embodiments of the invention are not limited to this.

Regions of attention may be set in frames in three or more directions. Furthermore, in the exemplified case, the regions of attention are set for the frames in two directions that are acquired while the C-arm is being rotated; however, embodiments of the invention are not limited to this. For example, in the case where the X-ray angiography apparatus 1 is a bi-plane type, regions of attention may be set in X-ray images in two directions each generated according to the X-ray detected by the x-ray detector 16 that is held by each a rm.

FIG. 4 will be referred back here. As described above, the regions of attention are set in the respective frames in at least two directions, and the depth region calculating unit 212 is able to set the above-described areas of attention by using various methods. A method of setting a region of attention by using the line of sight of the doctor, a method of setting a region of attention by using a fluoroscopic image, a method of directly setting a region of attention via the user terminal will be described sequentially.

Figures 7A, 7B:
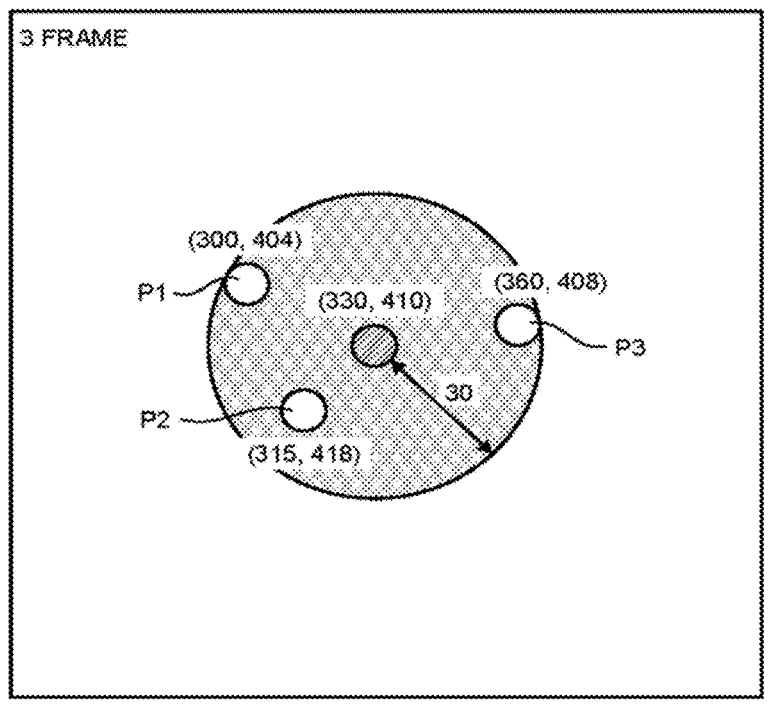
FIG. 7A is a diagram for explaining Example 1 of a region of attention setting processing performed by a depth region calculating unit according to the first embodiment.
FIG. 7B is a diagram for explaining Example 1 of the region of attention setting processing performed by the depth region calculating unit according to the first embodiment.

In the method of setting a region of attention by using the line of sight of the doctor, the depth region calculating unit 212 sets the area on the image that the operator gazes for the region of attention (setting region). Specifically, the depth region calculating unit 212 sets a region of attention by using information on the line of sight of the doctor received from the line-of-sight identifying device 400 via the communicating unit 28. FIGS. 7A and 7B are diagrams for explaining Example 1 of the region of attention setting processing performed by the depth region calculating unit 212 according to the first embodiment. As described above, the line-of-sight identifying device 400 converts the intersection between the plane of the display surface of the display unit 23a and the line of sight into the set of coordinates of the point in an arbitrary two-dimensional coordinate system formed on the display surface and transmits the set of coordinates to the operation terminal 200.

For example, as represented by "LINE-OF-SIGHT INFORMATION" shown in FIG. 7A, the line-of-sight identifying device 400 transmits, for each frame, information of the set of coordinates of the point gazed by the operator. For example, as shown in FIG. 7A, the line-of-sight identifying device 400 transmits the line-of-sight information of "FRAME: 3, (X-COORDINATE, Y-COORDINATE): (300, 404), (315,418), (360,408)" to the operation terminal 200. The information represents that, in "FRAME: 3", the doctor gazes the positions of the point at (300,404), the point at (315,418), and the point at (360,408) on the display unit 23a.

According to FIG. 7A, line-of-sight information is represented for only Frame 3 and Frame 24; however, practically, the line-of-sight identifying device 400 keeps acquiring information on the line of sight of the doctor during the display of the moving image and transmits the information to the operation terminal 200. In other words, the depth region calculating unit 212 sets a region of attention in each frame by performing the following processing on at least two frames from among the line-of-sight information acquired for all frames. Setting a region of attention in the Frame 3 will be exemplified below.

For example, as shown in FIG. 7A, the depth region calculating unit 212 sets region of attention information of "CENTER X-COORDINATE: 330, CENTER Y-COORDINATE: 410, and SIZE: 30" based on the line-of-sight information on "FRAME 3" of "(X-COORDINATE, Y-COORDINATE): (300,404), (315,418), and (360,408)". For example, as shown in FIG. 7B, the depth region calculating unit 212 sets, for the sets of coordinates of the center of the region of attention, (330,410) that is obtained by averaging the values of a point-of-view P1 (300,404), a point-of-view P2 (315,418), and a point-of-view P3 (360,408) acquired in "FRAME:3". The depth region calculating unit 212 then sets, for the size of the region of attention, a size of "30" by which the point of view most distant from the set of coordinates of the center is passed though. In other words, the depth region calculating unit 212 sets, for the region of attention, the minimum region containing all of the acquired points of view of the doctor. For the set of coordinates of the center, the most frequent value or the center value may be used, in addition to the average of the sets of coordinates of the points of views. Furthermore, for the size of the region of attention, dispersion of coordinates of the point of view or a standard deviation may be used.

The method of setting a region of attention by using the fluoroscopic image will be described here. In this case, for example, the depth region calculating unit 212 acquires the point of view of the doctor who is observing a fluoroscopic image and makes a setting as in the above-described case. In other words, the depth region calculating unit 212 sets of coordinates of the points of view acquired on the fluoroscopic image on the captured image that is captured at the same angle and sets a region of attention by using the sets of coordinates of the point of view, which are set, as in the case of the above-described example.

Figure 8:
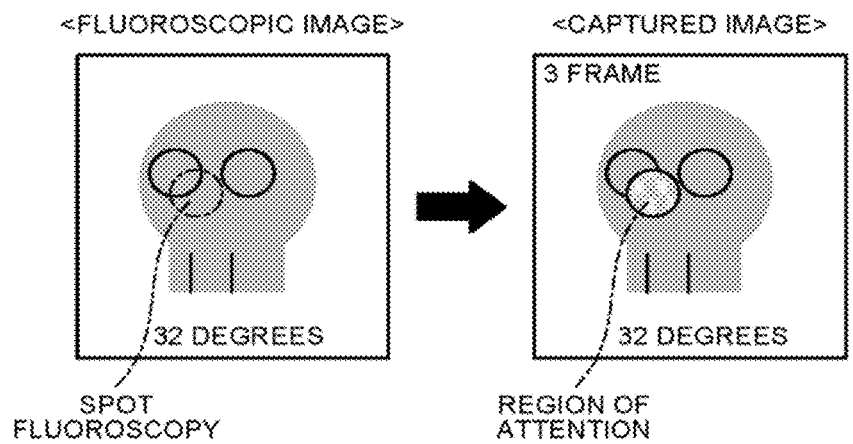
FIG. 8 is a diagram for explaining Example 2 of the region of attention setting processing performed by the depth region calculating unit according to the first embodiment.

When spot fluoroscopy in which an X-ray is emitted to only a predetermined region during fluoroscopy is performed, the depth region calculating unit 212 sets the predetermined region for the region of attention. FIG. 8 is a diagram for explaining Example 2 of the region of attention setting processing performed by the depth region calculating unit according to the first embodiment. For example, as shown in FIG. 8, when spot fluoroscopy is performed on a fluoroscopic image acquired at an angle of "32 DEGREES" of the C-arm 15, the depth region calculating unit 212 sets, for the region of attention, the same area of the captured image of the third frame acquired at the same angle of "32 DEGREES" of the C-arm 15 as that at which the fluoroscopic image is acquired.

Figure 9:
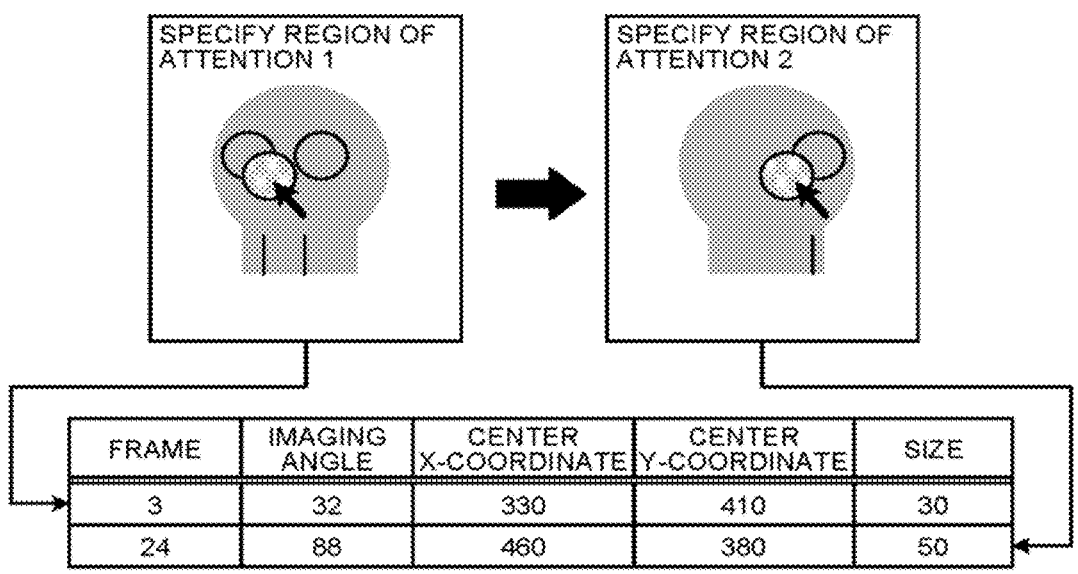
FIG. 9 is a diagram for explaining Example 3 of the region of attention setting processing performed by the depth region calculating unit according to the first embodiment.

The method of directly setting a region of attention via the user terminal will be described here. In this case, for example, the display controlling unit 211 causes the display unit 320 of the user terminal 300 to display X-ray images in at least two directions and sets, for the region of attention, a region that is accepted via the input unit 310. FIG. 9 is a diagram for explaining Example 3 of the region of attention setting processing performed by the depth region calculating unit according to the first embodiment. For example, as shown in FIG. 9, the display controlling unit 211 causes the display unit 320 (touch panel) of the user terminal 300 and accepts a region of attention setting. Here, as shown in FIG. 9, the display controlling unit 211 shows a message saying "SPECIFY REGION OF ATTENTION 1" together with the X-ray image in the first direction and shows a message saying "SPECIFY REGION OF ATTENTION 2" together with the X-ray image in the second direction. In this manner, a request for setting a region of attention can be clearly represented.

In the case of touch operation on the touch panel, it is difficult to finely specify coordinates. For this reason, the depth region calculating unit 212 may set, for the region of attention, a predetermined region covering the position of the touch operation. In the case where a region surrounding a predetermined region is specified, for example, the depth region calculating unit 212 may set, for the region of attention, a region having an arbitrary size covering a predetermined region.

FIG. 9 exemplifies the case where the X-ray image is displayed on the display unit 320 of the user terminal 300 and the region of attention is set by touch operation. Alternatively, the display unit 23a in the examination room R1 may be caused to display the X-ray image and the region of attention may be set on the display unit 23a. In this case, for example, the pointer on the display unit 23a is operated by using the touch panel of the user terminal 300 to set the region of attention on the X-ray image displayed by the display unit 23a.

Figure 10A:
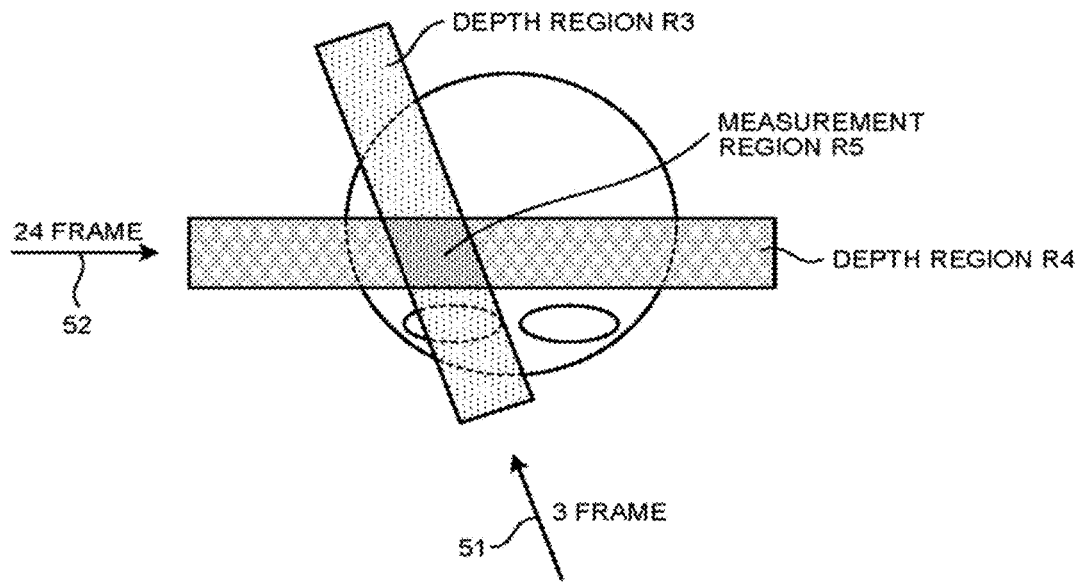
FIG. 10A is a diagram for explaining calculation of a measurement region performed by a measurement region calculating unit according to the first embodiment.
Figure 10B:
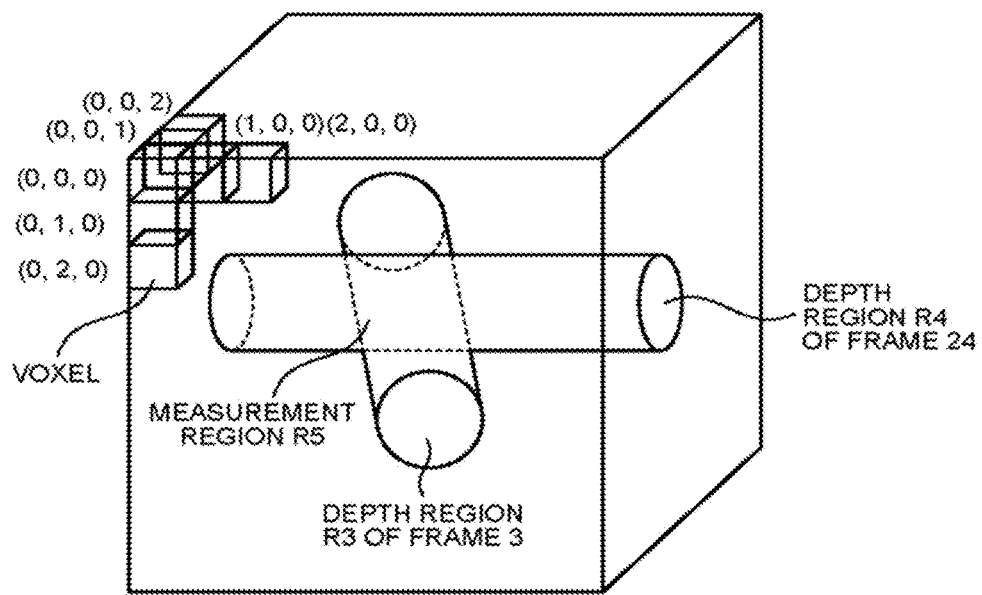
FIG. 10B is a diagram for explaining calculation of the measurement region performed by the measurement region calculating unit according to the first embodiment.

Once the region of attention is set by using any one of the above-described various methods, the depth region calculating unit 212 calculates each of depth regions that are three-dimensional regions obtained by extending the respective regions of attention in depth directions on the volume data. The measurement region calculating unit 213 calculates, for a region of interest (measurement region), a region where the calculated depth regions overlap. In other words, the measurement region calculating unit 213 calculates measurement region (a region of interest in a three dimensional medical image data on a subject). FIGS. 10A and 10B are diagrams for explaining calculation of the measurement region calculated by the measurement region calculating unit 213 according to the first embodiment. For example, as shown in FIG. 10A, the depth region calculating unit 212 calculates a depth region R3 obtained by extending the region of attention set in the third frame in a depth direction 51 in the image of the third frame. Similarly, the depth region calculating unit 212 calculates a depth region R4 obtained by extending the region of attention set in the 24th frame in a depth direction 52 in the image of the 24th frame.

As shown in FIG. 10A, the measurement region calculating unit 213 calculates the area where the depth region R3 and the depth region R4 overlap as a measurement region R5. As described above, the regions of attention are represented by the sets of coordinates on the display surface of the display unit 23a. Accordingly, the depth region calculating unit 212 first acquires the sets of coordinates of the volume data corresponding to the regions of attention. In other words, as for the coordinates on the display unit 23a, the depth region calculating unit 212 acquires information on the sets of coordinates in the volume data of the image that is output from the pixels of the coordinates at which the region of attentions are displayed. For example, as shown in FIG. 10B, the depth region calculating unit 212 calculates the sets of coordinates of the voxels corresponding to the region of attention R1 of the frame 3 and calculates the depth region R3 obtained by extending the group of voxels at the calculated sets of coordinates in the depth direction. Similarly, for example, as shown in FIG. 10B, the depth region calculating unit 212 calculates the sets of coordinates of the voxels corresponding to the region of attention R2 of the frame 24 and calculates the depth region R4 obtained by extending the group of voxels at the calculated sets of coordinates in the depth direction.

The measurement region calculating unit 213 then calculates the measurement region R5 that is the region where the depth region R3 and the depth region R4 overlap. In other words, the measurement region calculating unit 213 calculates, as the measurement region R5, a group of voxels contained in the depth region R3 and the depth region R4. FIGS. 10A and 10B exemplify the case where the region where the two depth regions overlap serves as the measurement region; however, when three or more depth regions are calculated, the measurement region calculating unit 213 calculates the group of voxels contained in all of the depth regions as the measurement region.

Figure 11:
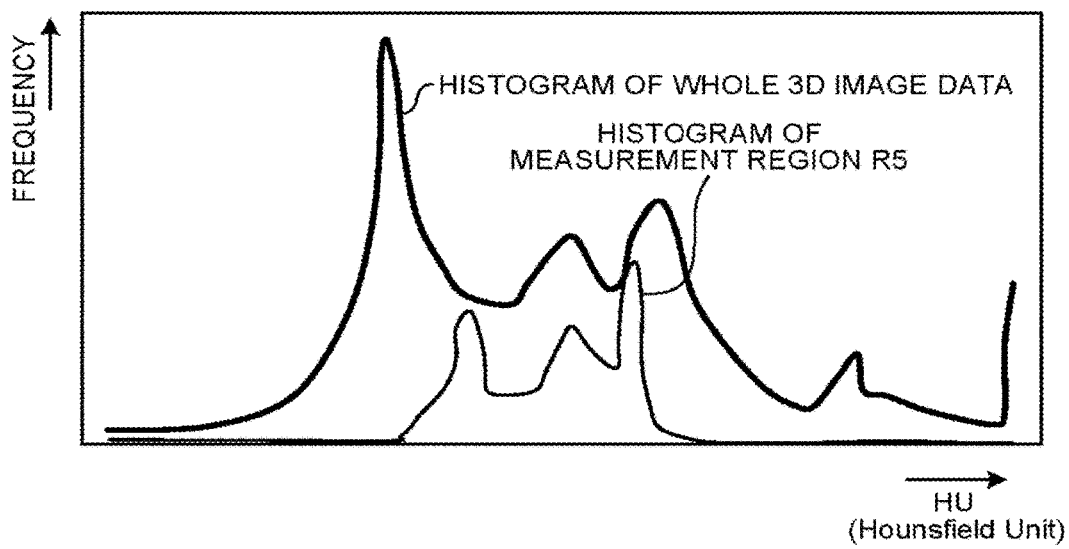
FIG. 11 is a diagram of an exemplary histogram that is calculated by a histogram calculating unit according to the first embodiment.

FIG. 4 will be referred back here. The histogram calculating unit 214 calculates a histogram based on the volume data. Specifically, the histogram calculating unit 214 calculates a histogram of the whole volume data and a histogram of the measurement region calculated by the measurement region calculating unit 213. FIG. 11 is a diagram of an exemplary histogram that is calculated by the histogram calculating unit 214 according to the first embodiment. FIG. 11 shows a histogram where the horizontal axis represents the Hounsfield unit (HU) representing the X-ray absorption coefficient and the vertical axis represents the degree. For example, as shown in FIG. 11, the histogram calculating unit 214 calculates a histogram of the whole three-dimensional image data (volume data) and a histogram of the measurement region R5.

FIG. 4 will be referred back here. The examination device information acquiring unit 215 acquires the examination information stored in the examination information storage unit 272 and device information stored in the device information storage unit 273. Specifically, the examination device information acquiring unit 215 acquires the current examination information on the subject and current device information on the apparatus main unit 100 and transmits the current examination information and the current device information to the opacity curve candidate calculating unit 216.

The opacity curve candidate calculating unit 216 calculates a parameter value relating to the image processing on the medical image that is generated from the three-dimensional image data, on the basis of the voxel values of the measurement region. Specifically, on the basis of the voxel values of the measurement region, the opacity curve candidate calculating unit 216 calculates a parameter setting value for making an opacity setting for the medical image that is generated from the three-dimensional image data. More specifically, the opacity curve candidate calculating unit 216 determines a parameter setting candidate (candidate of opacity curve) for making an opacity setting for the medical image that is generated from the volume data. For example, the opacity curve candidate calculating unit 216 determines an area for which the opacity is varied in the histogram of the voxel values of the measurement region and a pattern for varying the opacity in the area.

Figure 12:
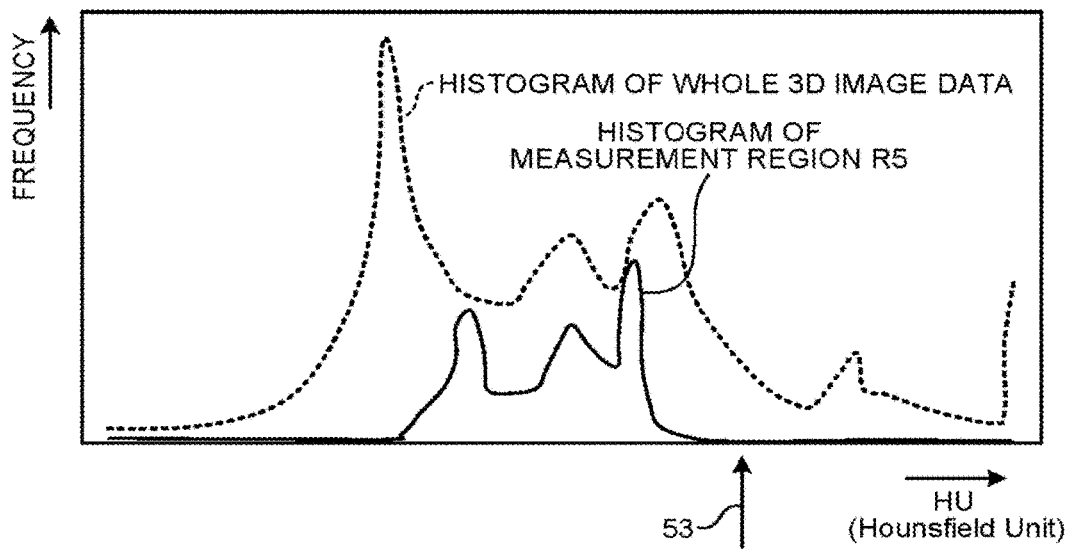
FIG. 12 is a diagram for explaining processing of determining an excluded area performed by an opacity curve candidate calculating unit according to the first embodiment.

For example, the opacity curve candidate calculating unit 216 determines an area to be excluded from an area for which a parameter is set by using the histogram of the voxel values of the volume data. FIG. 12 is a diagram for explaining processing of determining the area to be excluded, which is processing performed by the opacity curve candidate calculating unit 216 according to the first embodiment. For example, the opacity curve candidate calculating unit 216 determines, as the area to be excluded from the area for which the opacity curve is set, an area where the HU is higher than that denoted by the arrow 53 shown in FIG. 12. For example, bones have "HU: 200 to 1000". In order to remove bones from the image, the opacity curve candidate calculating unit 216 excludes the area where the HU is higher than that denoted by the arrow 53 from the area for which the opacity curve is set.

Figure 13:
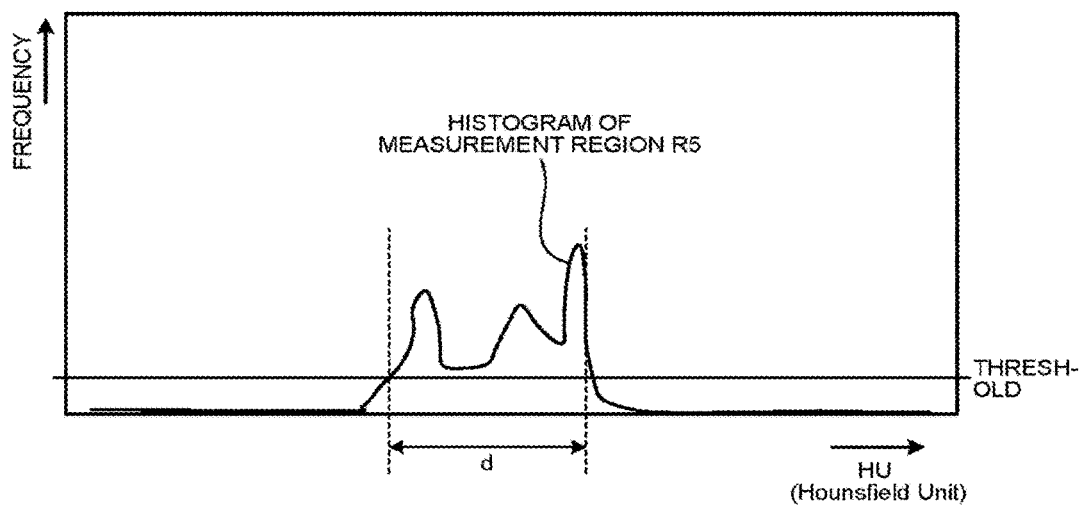
FIG. 13 is a diagram for explaining exemplary area setting performed by the opacity curve candidate calculating unit according to the first embodiment.

For example, the opacity curve candidate calculating unit 216 determines, as an area for which the opacity is varied, an area where a threshold of frequency that is set based on the type of the measurement region in the histogram of voxel values of the measurement region is exceeded. FIG. 13 is a diagram for explaining an exemplary area setting made by the opacity curve candidate calculating unit 216 according to the first embodiment. For example, as shown in FIG. 13, the opacity curve candidate calculating unit 216 determines an area "d" where the frequency exceeds a preset threshold as an area for which the opacity is varied.

The opacity curve candidate calculating unit 216 determines a site to be examined according to examination information (such as examination protocols) on the examination that is being carried out and the device information (such as the positions of the C-arm 15 and the couchtop 14) at the time when imaging is performed, reads the threshold that is preset for the determined site, and determines an area. For example, a high threshold is preset for a site not containing various tissues (such as brain), and a low threshold is preset for a site containing various tissues (such as abdomen). This is because, when the site does not contain various tissues, voxel values similar to one another are represented and thus a high threshold can be set, meanwhile, when the site contains various tissues and if a high threshold is set, the internal organ to be examined may be out of the area.

Figure 14:
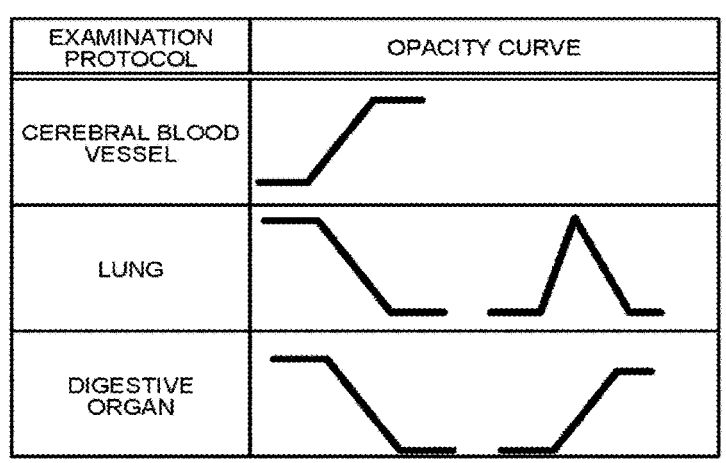
FIG. 14 is a table illustrating exemplary opacity curve patterns according to the first embodiment.

The opacity curve candidate calculating unit 216 determines a pattern of opacity curve according to the type of a site that is a subject. FIG. 14 is a diagram illustrating exemplary patterns of opacity curve according to the first embodiment. For example, as shown in FIG. 14, information in which the patterns of opacity curve to be applied are associated with the respective examination protocols (such as cerebral blood vessel, lung, and digestive organ) is preset, and the opacity curve candidate calculating unit 216 reads a pattern of opacity curve that is associated with the current examination protocol, and determines an opacity curve candidate by setting the pattern for the determined area.

Figure 15A:
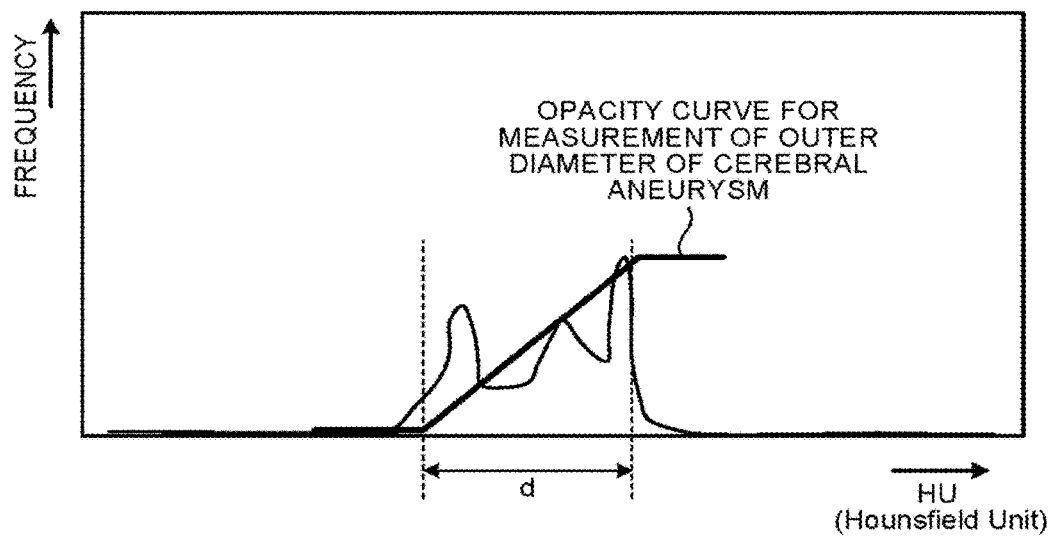
FIG. 15A is a diagram illustrating an exemplary candidate of opacity curve that is determined by an opacity curve candidate calculating unit according to the first embodiment.
Figure 15B:
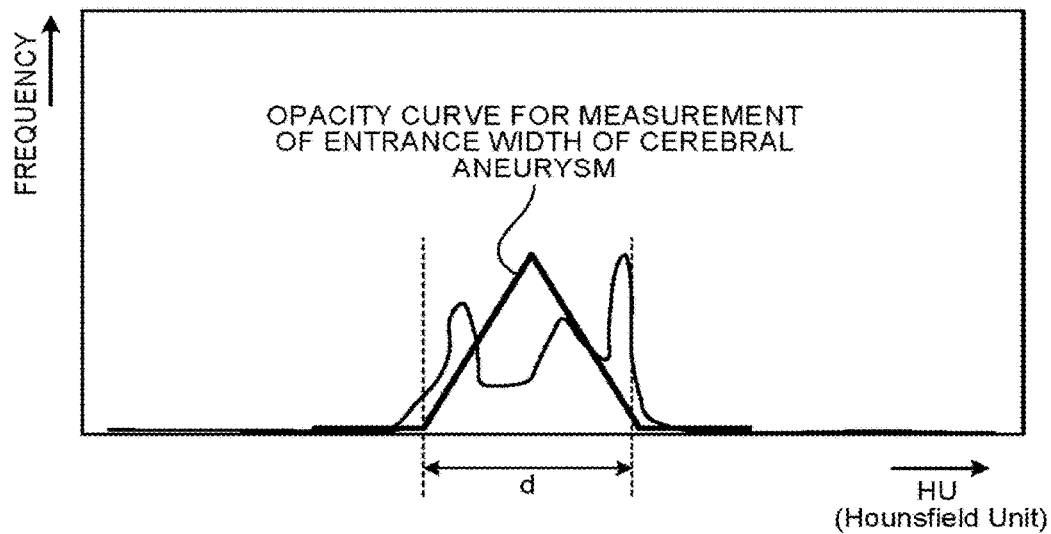
FIG. 15B is a diagram illustrating an exemplary candidate of opacity curve that is determined by the opacity curve candidate calculating unit according to the first embodiment.

FIGS. 15A and 15B are diagrams illustrating exemplary candidates of opacity curve that are determined by the opacity curve candidate calculating unit 216 according to the first embodiment. FIGS. 15A and 15B show candidates of opacity curve obtained by setting opacity curves of different patterns in the area that is set as shown in FIG. 13. For example, as shown in FIG. 15A, the opacity curve candidate calculating unit 216 determines an opacity curve candidate obtained by setting an opacity curve of a pattern rising in the area "d". Furthermore, as shown in FIG. 15B, for example, the opacity curve candidate calculating unit 216 determines an opacity curve candidate obtained by setting an opacity curve of a pattern triangular in the area "d".

FIGS. 15A and 15B exemplify the cases where the opacity curves of the different patterns are set, respectively. Alternatively, the opacity curve candidate calculating unit 216 may determine opacity curve candidates of the same pattern that have different obliqueness. For example, the opacity curve candidate calculating unit 216 may determine an opacity curve candidate obtained by setting an opacity curve of the rising pattern shown in FIG. 15A having a small obliqueness in the area "d".

Figure 16:
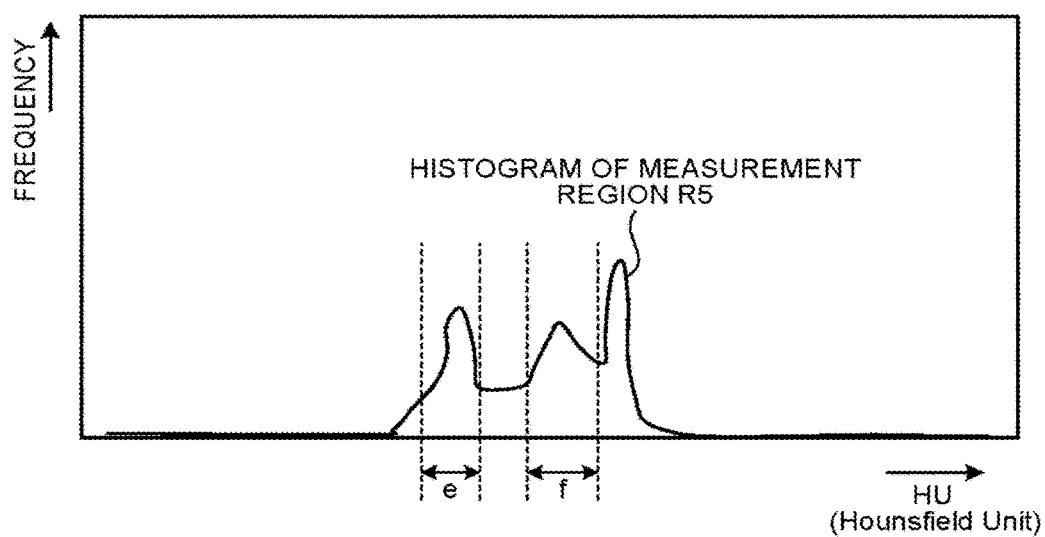
FIG. 16 is a diagram for explaining an exemplary area setting made by the opacity curve candidate calculating unit according to the first embodiment.

The opacity curve candidate calculating unit 216 may determine the band of the voxel values corresponding to the type of the measurement region as the area for which the opacity is varied. FIG. 16 is a diagram for explaining an exemplary area setting made by the opacity curve candidate calculating unit 216 according to the first embodiment. For example, as shown in FIG. 16, the opacity curve candidate calculating unit 216 determines an area "e" corresponding to vascular walls and an area "f" corresponding to the inside of blood vessels as the area for which the opacity is varied.

Figure 17A:
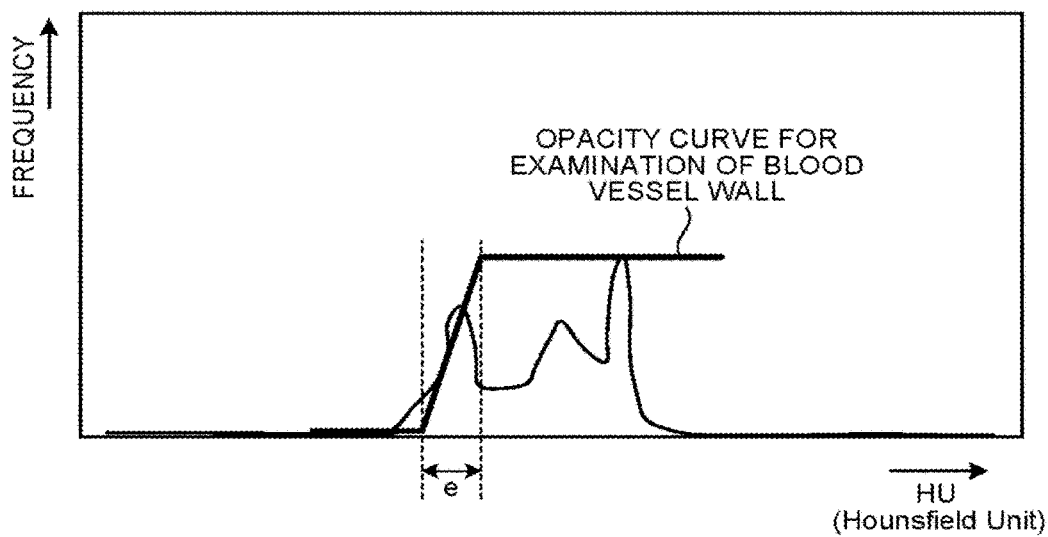
FIG. 17A is a diagram illustrating an exemplary opacity curve candidate that is determined by the opacity curve candidate calculating unit according to the first embodiment.
Figure 17B:
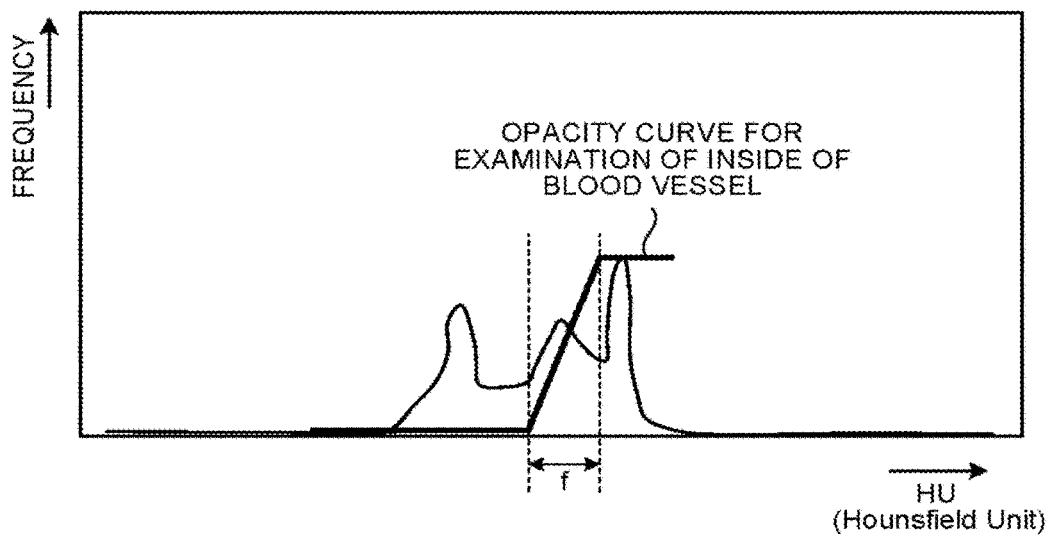
FIG. 17B is a diagram illustrating an exemplary opacity curve candidate that is determined by the opacity curve candidate calculating unit according to the first embodiment.

The opacity curve candidate calculating unit 216 determines opacity curve candidates for the respective areas that are set. FIGS. 17A and 17B are diagrams illustrating exemplary opacity curve candidates that are determined by the opacity curve candidate calculating unit 216 according to the first embodiment. For example, as shown in FIG. 17A, the opacity curve candidate calculating unit 216 determines an opacity curve candidate obtained by setting an opacity of a rising pattern in the area "d". Furthermore, for example, as shown in FIG. 17B, the opacity curve candidate calculating unit 216 determines an opacity curve candidate obtained by setting an opacity curve of a rising pattern in the area "f".

Once opacity curve candidates are determined as shown in FIGS. 15A and 15B and FIGS. 17A and 17B, the display controlling unit 211 presents, to the operator, at least any one of the parameter setting candidate that is determined by the opacity curve candidate calculating unit 216 and the medical image obtained by generating a three-dimensional image from the volume data on the basis of the parameter setting candidate. In other words, once the opacity curve candidate calculating unit 216 determines a parameter setting candidate, the image reconstructing unit 25 generates a three-dimensional image based on the parameter setting candidate. The display controlling unit 211 presents at least one of the parameter setting candidate and the three-dimensional image to the operator. For example, the display controlling unit 211 performs control to display only the opacity curve candidate, only the three-dimensional image based on the opacity curve candidate, or both of the opacity curve candidate and the three-dimensional image on the display unit 320 of the user terminal 300.

Figure 18A:
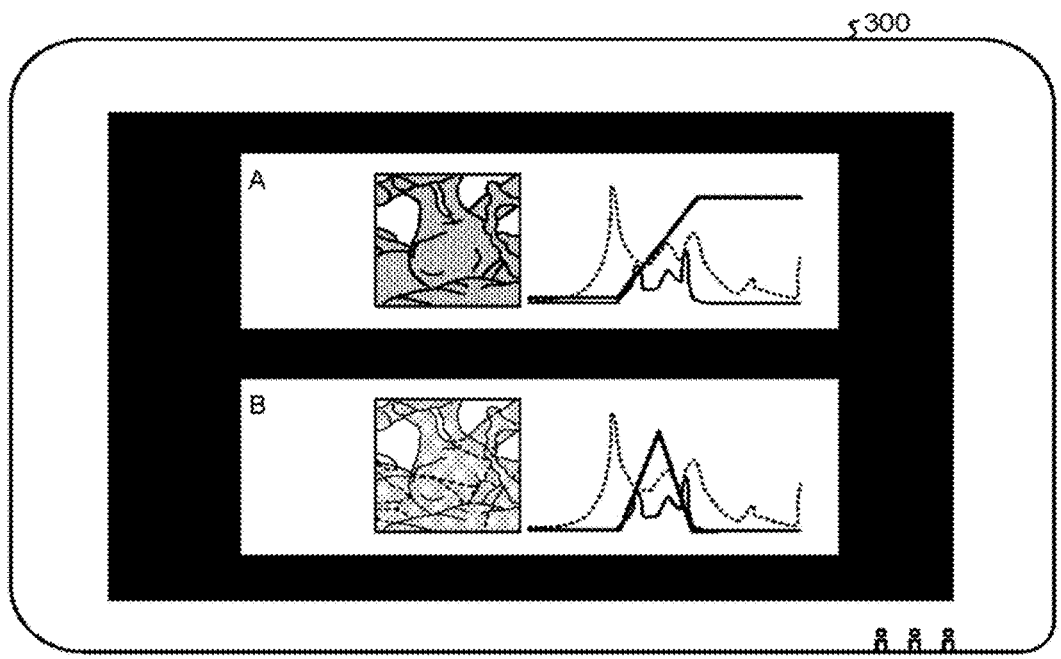
FIG. 18A is a diagram illustrating exemplary information represented by the display controlling unit according to the first embodiment.
Figure 18B:
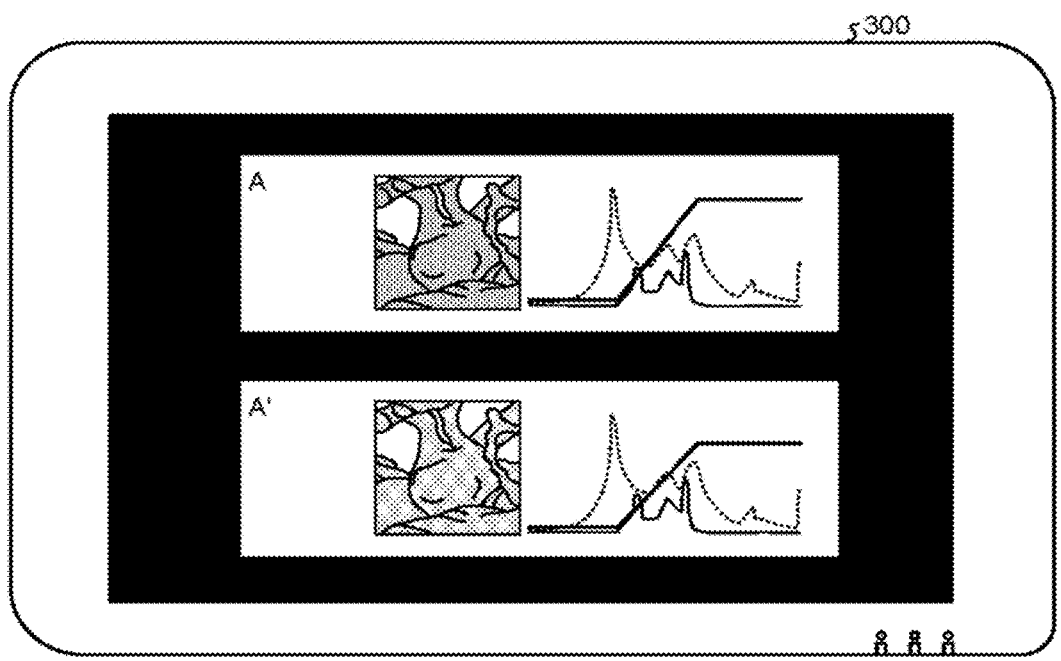
FIG. 18B is a diagram illustrating exemplary information represented by the display controlling unit according to the first embodiment.

FIGS. 18A and 18B are diagrams illustrating exemplary information presented by the display controlling unit 211 according to the first embodiment. FIG. 18 shows an example where information is represented to the user terminal 300. As shown in FIG. 18(A), the display controlling unit 211 displays the opacity curve candidate "A" obtained by setting a rising opacity curve and the opacity curve candidate "B" obtained by setting a triangular pattern together with images. This allows the doctor to recognize at a glance the opacity curve setting and what kind of image will be generated according to the opacity curve setting to easily make an easy-to-see display even in the examination room. The information displayed on the user terminal 300 may be any one of the opacity curve candidate or the image. For example, only the opacity curve candidates, or only the images, of the candidate "A" and the candidate "B" shown in FIG. 18(A) may be displayed.

Furthermore, for example, when the doctor selects the opacity curve candidate "A" through a touch operation, the display controlling unit 211 displays together, as shown in FIG. 18(B), the opacity curve candidate "A" and an opacity curve candidate "A'" that is obtained by setting a rising opacity curve and that has obliqueness different from that of the opacity curve candidate "A". In other words, by accepting the opacity curve candidate "A" selected by the doctor, the image reconstructing unit 25 selects the opacity curve candidate "A'" relating to the opacity curve candidate "A" and generates a three-dimensional image based on the selected opacity curve candidate "A'". The display controlling unit 211 then displays the opacity curve candidate "A" and the opacity curve candidate "A'" together. This allows the doctor to easily make a more easy-to-see display of the image. The information presented to the user terminal 300 at this stage may be any one of the opacity curve candidate and the image. For example, as for "A" and "A'" shown in FIG. 18B, only the opacity curve candidates or only the images may be displayed.

Figure 19:
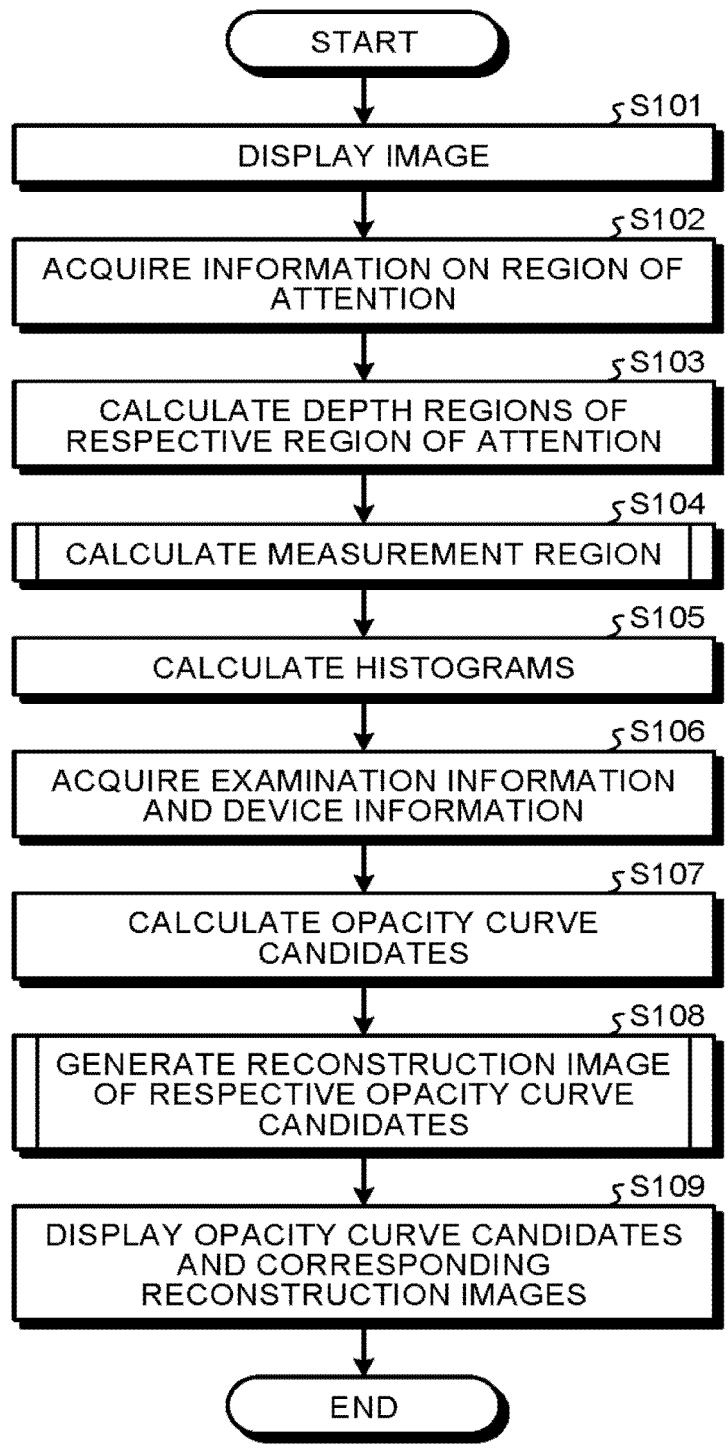
FIG. 19 is a flowchart of a procedure of processing performed by the X-ray angiography apparatus according to the first embodiment.
Figure 20:
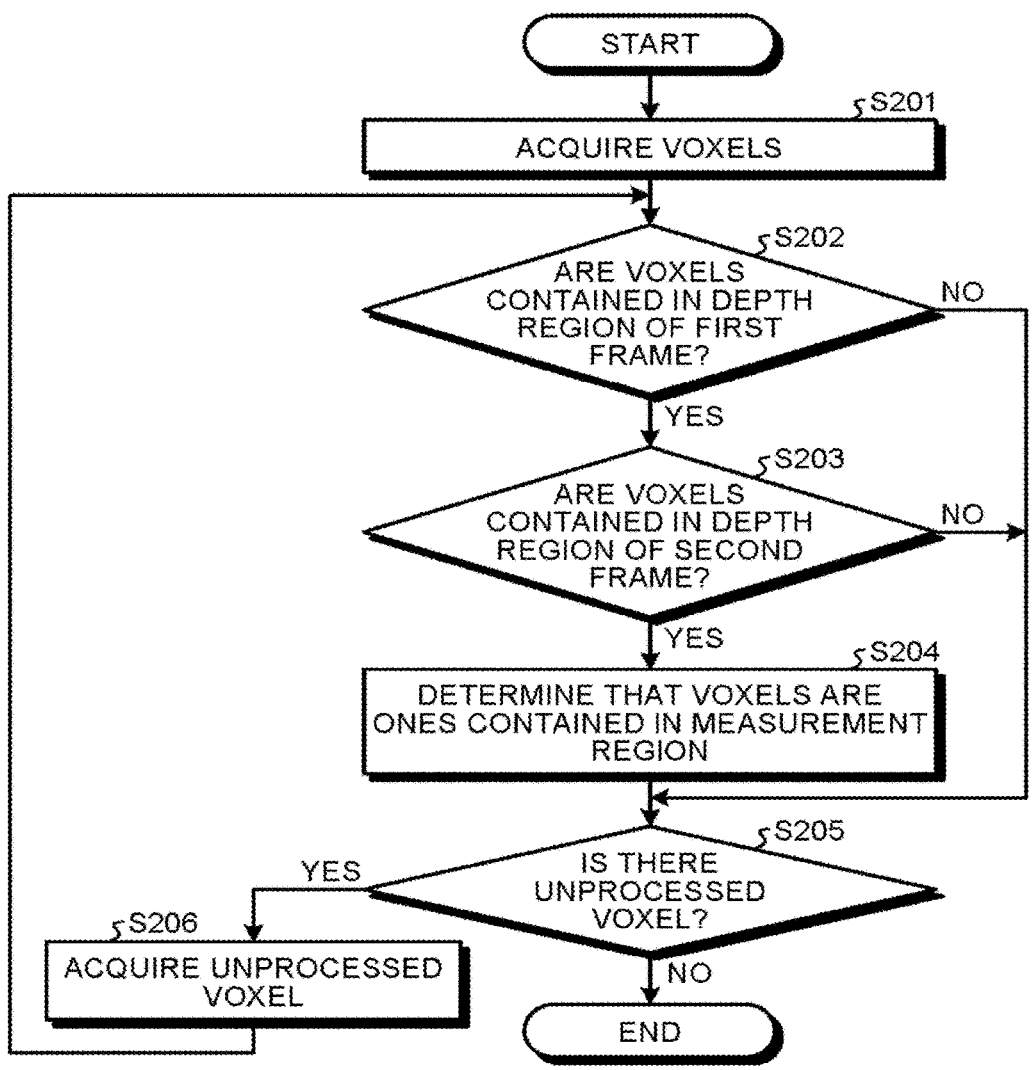
FIG. 20 is a flowchart of the procedure of processing performed by the X-ray angiography apparatus according to the first embodiment.
Figure 21:
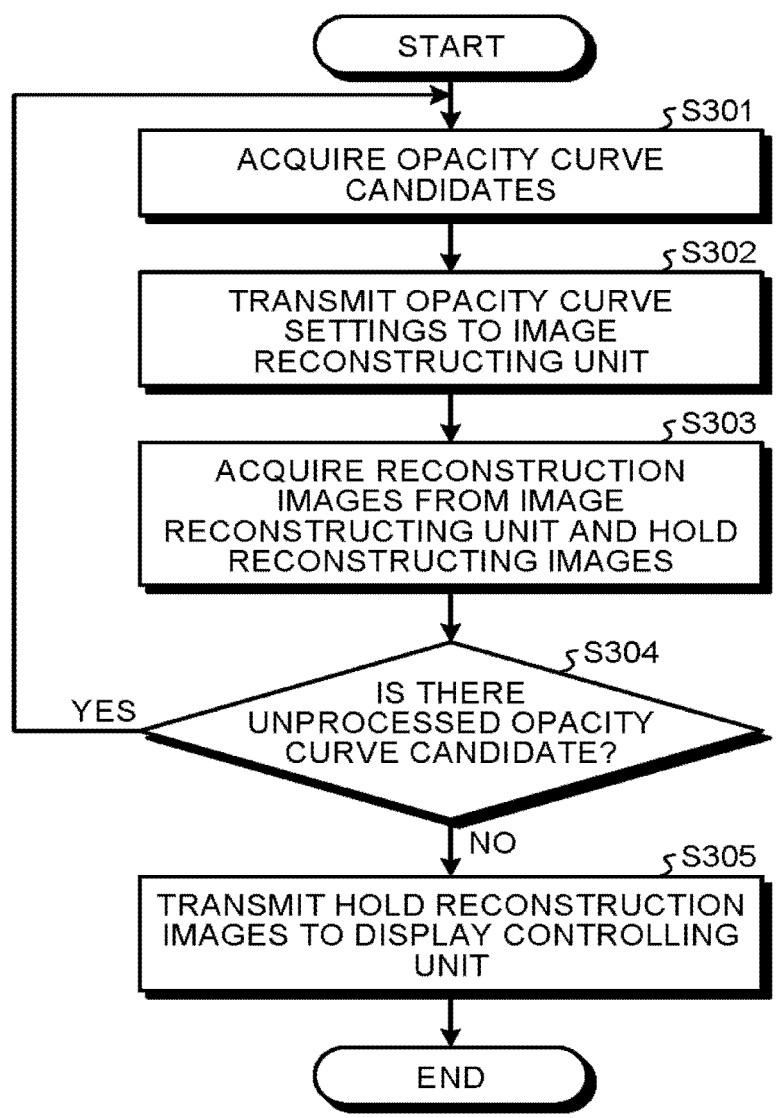
FIG. 21 is a flowchart of the procedure of processing performed by the X-ray angiography apparatus according to the first embodiment.

With reference to FIGS. 19 to 21, the processing performed by the X-ray angiography apparatus 1 according to the first embodiment will be described. FIGS. 19 to 21 are flowcharts of a procedure of the processing performed by the X-ray angiography apparatus 1 according to the first embodiment. FIG. 19 illustrates the procedure of the whole processing performed by the X-ray angiography apparatus 1, FIG. 20 illustrates the detailed processing at step S104 shown in FIG. 19, and FIG. 21 illustrates the detailed processing at step S108 shown in FIG. 19. The processing will be described sequentially below.

As shown in FIG. 19, in the X-ray angiography apparatus 1 according to the first embodiment, once the display controlling unit 211 displays an image (step S101), the depth region calculating unit 212 acquires information on region of attention (step S102). For example, the depth region calculating unit 212 acquires information on the line of sight of a doctor and setting information for the image. The depth region calculating unit 212 calculates depth regions based on the acquired information (step S103).

The measurement region calculating unit 213 then calculates a measurement region based on the depth regions calculated by the depth region calculating unit 212 (step S104). The histogram calculating unit 214 then calculates histograms (step S105) and the examination device information acquiring unit 215 acquires examination information and device information (step S106). The opacity curve candidate calculating unit 216 then calculates opacity curve candidates (step S107).

The image reconstructing unit 25 generates reconstruction images of the respective opacity curve candidates on the basis of the opacity curve candidates determined by the opacity curve candidate calculating unit 216 (step S108) and the display controlling unit 211 displays the opacity curve candidates and the corresponding reconstruction images to the doctor (step S109).

In the X-ray angiography apparatus 1 according to the first embodiment, when a measurement region is calculated, as shown in FIG. 20, the measurement region calculating unit 213 acquires voxels (step S201) and determines whether the acquired voxels are contained in the depth region of a first frame (step S202). Upon determining that the acquired voxels are contained in the depth region of the first frame (YES at step S202), the measurement region calculating unit 213 determines whether the acquired voxels are contained in the depth region of a second frame (step S203). Upon determining that the acquired voxels are contained also in the depth region of the second frame (YES at step S203), the measurement region calculating unit 213 determines that the acquired voxels are voxels contained in the measurement region.

The measurement region calculating unit 213 determines whether there is an unprocessed voxel (step S205). When there is an unprocessed voxel (YES at step S205), the measurement region calculating unit 213 acquires the unprocessed voxel (step S206) and performs the determination processing at step S202. On the other hand, when there is no unprocessed voxel (NO at step S205), the measurement region calculating unit 213 ends the processing. At step S202 or step S203, when the acquired voxels are not contained in the depth region (NO at step S202 or NO at step S203), the measurement region calculating unit 213 performs the determination processing at step S205.

In the X-ray angiography apparatus 1 according to the first embodiment, when reconstruction images corresponding to the respective opacity curve candidates are generated, as shown in FIG. 21, the system controlling unit 21 acquires opacity curve candidates (step S301) and transmits opacity curve settings to the image reconstructing unit 25 (step S302). The system controlling unit 21 acquires and holds reconstruction images from the image reconstructing unit 25 (step S303) and determines whether there is an unprocessed opacity curve (step S304).

Upon determining that there is an unprocessed opacity curve (YES at step S304), the system controlling unit 21 goes back to step S301 and performs the processing. On the other hand, upon determining that there is no unprocessed opacity curve (NO at step S304), the system controlling unit 21 transmits the reconstruction images that the system controlling unit 21 holds to the display controlling unit 211 (step S305).

As described above, according to the first embodiment, the measurement region calculating unit 213 calculates a measurement region in a three-dimensional medical image data on a subject, on the basis of the setting region (the regions of attention) that are set in the respective images in at least two directions acquired from the subject. On the basis of the voxel values of the measurement region, the opacity curve candidate calculating unit 216 calculates a parameter setting value for making an opacity setting for the medical image generated from the three-dimensional medical image data. Accordingly, the X-ray angiography apparatus 1 according to the first embodiment makes it easy to make a display of an easy-to-observe image.

Furthermore, according to the first embodiment, the opacity curve candidate calculating unit 216 calculates a parameter setting value by using the histogram of the voxel values of the measurement region. Accordingly, the X-ray angiography apparatus 1 according to the first embodiment makes it possible to make a proper opacity setting for the medical image.

According to the first embodiment, the display controlling unit 211 represents, to the operator, at least one of the parameter setting value calculated by the opacity curve candidate calculating unit 216 and the medical image generated from the three-dimensional medical image data in accordance with the parameter setting value. Accordingly, the X-ray angiography apparatus 1 according to the first embodiment makes it easy to display a medical image for which an opacity setting desired by the operator is made.

According to the first embodiment, the opacity curve candidate calculating unit 216 determines, as a parameter setting candidate, an area for which the opacity is varied in the histogram of the voxel values of the measurement region and the pattern for varying the opacity in the area. The opacity curve candidate calculating unit 216 determines, as the area for which the opacity is varied, the area in which the threshold of frequency that is set based on the type of the measurement region in the histogram of the voxel values of the measurement region. The opacity curve candidate calculating unit 216 determines the band of the voxel values corresponding to the type of the measurement region as the area for which the opacity is varied. The opacity curve candidate calculating unit 216 determines an area to be excluded from the area for which the parameter is set by using the histogram of the voxel values in the three-dimensional image data. Accordingly, the X-ray angiography apparatus 1 according to the first embodiment makes it possible to flexibly set an opacity curve depending on the case.

According to the first embodiment, the measurement region calculating unit 213 calculates depth regions that are three-dimensional regions obtained by extending a setting region on a three-dimensional image data in depth directions and calculates, as a measurement region, a region where the calculated depth regions overlap. According, the X-ray angiography apparatus 1 according to the first embodiment makes it possible to accurately calculate the measurement region.

According to the first embodiment, the system controlling unit 21 accepts a setting region setting for the medical images in at least two directions. On the basis of the setting information accepted by the system controlling unit 21, the measurement region calculating unit 213 calculates a measurement region. The system controlling unit 21 accepts the region that is focused by the operator for each of the medical images in at least two directions. Accordingly, the X-ray angiography apparatus 1 according to the first embodiment makes it easy to calculate the measurement region desired by the operator.

According to the first embodiment, the system controlling unit 21 receives, as the setting region, at least one of the region gazed by the operator during radiography using X-rays and a region for which spot radiography is performed. The measurement region calculating unit 213 calculates the measurement region on the subject imaged by using X-rays, based on the setting region accepted by the system controlling unit 21. Accordingly, the X-ray angiography apparatus 1 according to the first embodiment can set a measurement region by using a fluoroscopic image.

Second Embodiment

The first embodiment has been described above. The present invention may be carried out as various different embodiments in addition to the first embodiment.

The first embodiment has been described above by exemplifying the case where opacity curve candidates are presented to an operator and the operator selects a desired opacity curve; however, embodiments of the invention are not limited to this. For example, instead of presenting opacity curve candidates, an opacity curve may be determined and then an image may be displayed. In this case, the opacity curve candidate calculating unit 216 determines an opacity curve and, according to the determined opacity curve, the image reconstructing unit 25 generates a reconstruction image, such as a volume rendering image or an MPR image. The display controlling unit 211 displays the generated reconstruction image on, for example, the display unit 23a or the display unit 23b.

The first embodiment has been described by exemplifying the case where opacity is used as a parameter value relating to image processing on a medical image; however, embodiments of the invention are not limited to this. For example, color, scaling up/down or direction may be used instead. Exemplary cases where color, scaling up/down and direction are respectively used as parameter values relating to image processing on medical images will be described sequentially below.

First, the case where color is used as a parameter value relating to image processing on a medical image will be described. In this case, for example, the color of a measurement region may be enhanced and displayed. For example, the display controlling unit 211 colors a measurement region that is generated by the image reconstructing unit 25 to display a three-dimensional image having the enhanced measurement region. Accordingly, it is possible to display a three-dimensional image where, for example, a tumor contained in the measurement region is enhanced.

When color is used as the parameter value relating to image processing, after a given site is extracted by performing the image processing, the extracted given site may be colored. For example, the image processing unit 26 may extract blood vessels by performing image processing by using, for example, various applications on the measurement region (measurement region) and may further extract an aneurysm or a site of stenosis from the extracted blood vessels. The display controlling unit 211 colors the aneurysm or the site of stenosis in the three-dimensional image generated by the image reconstructing unit 25 to display a three-dimensional image where the aneurysm or the site of stenosis is enhanced. Accordingly, for example, a part to which attention is further paid in the measurement region can be easily known.

The case where scaling up/down is used as a parameter value relating to image processing on medical image will be described here. In this case, for example, a tumor, a cerebral aneurysm, or a site of stenosis can be displayed in a size so as to be easily viewed. For example, the image processing unit 26 extracts a site, such as a tumor, cerebral aneurysm, or a site of stenosis, by performing image processing by using, for example, various applications on the measurement region. The display controlling unit 211 scales up or scales down the three-dimensional image into a given display size in which the site is easily viewed and displays the image. The display sizes of the respective sites are preset and stored in the storage unit 27. In other words, the display controlling unit 211 reads the display size corresponding to the site extracted by the image processing unit 26 from the storage unit 27 and scales up or scales down the three-dimensional image to be in the read size and displays the three-dimensional image. The site extracted by the image processing unit 26 is then identified according to the type of the used application, etc. In this manner, each site can be displayed in the best display size, so that an easy-to-see three-dimensional image can be displayed.

The case where direction is used as a parameter value relating to image processing on a medical image will be described below. In this case, for example, a tumor, cerebral aneurysm, or a site of stenosis can be displayed to be in a direction so as to be easy to check. For example, the image processing unit 26 performs image processing by using various applications on the measurement region to extract blood vessels and further extract the site of stenosis from the extracted blood vessels. The display controlling unit 211 displays the three-dimensional image of the extracted site of stenosis generated in the direction in which the site of stenosis is easy to check. For example, when the image processing unit 26 extracts a site of stenosis, the image reconstructing unit 25 determines the state where the site of stenosis positions in the volume data (the direction in which the blood vessel containing the site of stenosis runs). When the image reconstructing unit 25 observes the site of stenosis panoramically about the determined direction in which the blood vessel runs, the image reconstructing unit 25 specifies a direction in which the blood vessels are most finely observed. Furthermore, the image reconstructing unit 25 generates a three-dimensional image by performing rendering processing in the specified direction. The display controlling unit 211 displays the generated three-dimensional image. The display controlling unit 211 displays the generated three-dimensional image. In this manner, an image optimum to diagnosis can be displayed.

As described above, the second embodiment has been described by exemplifying the cases where color, scaling up/down and direction are respectively used as parameter values relating to image processing on medical images. For the second embodiment, the cases where color, scaling up/down and direction are respectively used have been described separately; however, embodiments of the invention are not limited to this. Color, scaling up/down and direction may be used in combination as appropriate. Color, scaling up/down and direction may be used in combination also for opacity.

The embodiments have been described by exemplifying the case where the X-ray angiography apparatus is used as the medical image diagnosis apparatus; however, embodiments of the invention are not limited to this. For example, an X-ray CT apparatus may be used.

The various components of various devices according to the first embodiment that are shown in the drawings are functional ideas and thus are not necessarily physically configured as shown in the drawings. In other words, specific modes of separation and integration between components are not limited to that shown in the drawings. Whole or part of the devices may be separated or integrated functionally or physically in an arbitrary unit according to various loads or the situation where the devices are used. Furthermore, whole or an arbitrary part or various processing functions implemented by various devices may be implemented by a CPU and a program that is analyzed and executed by the CPU or implemented as a hard wired logic.

Other Embodiments

Figure 22:
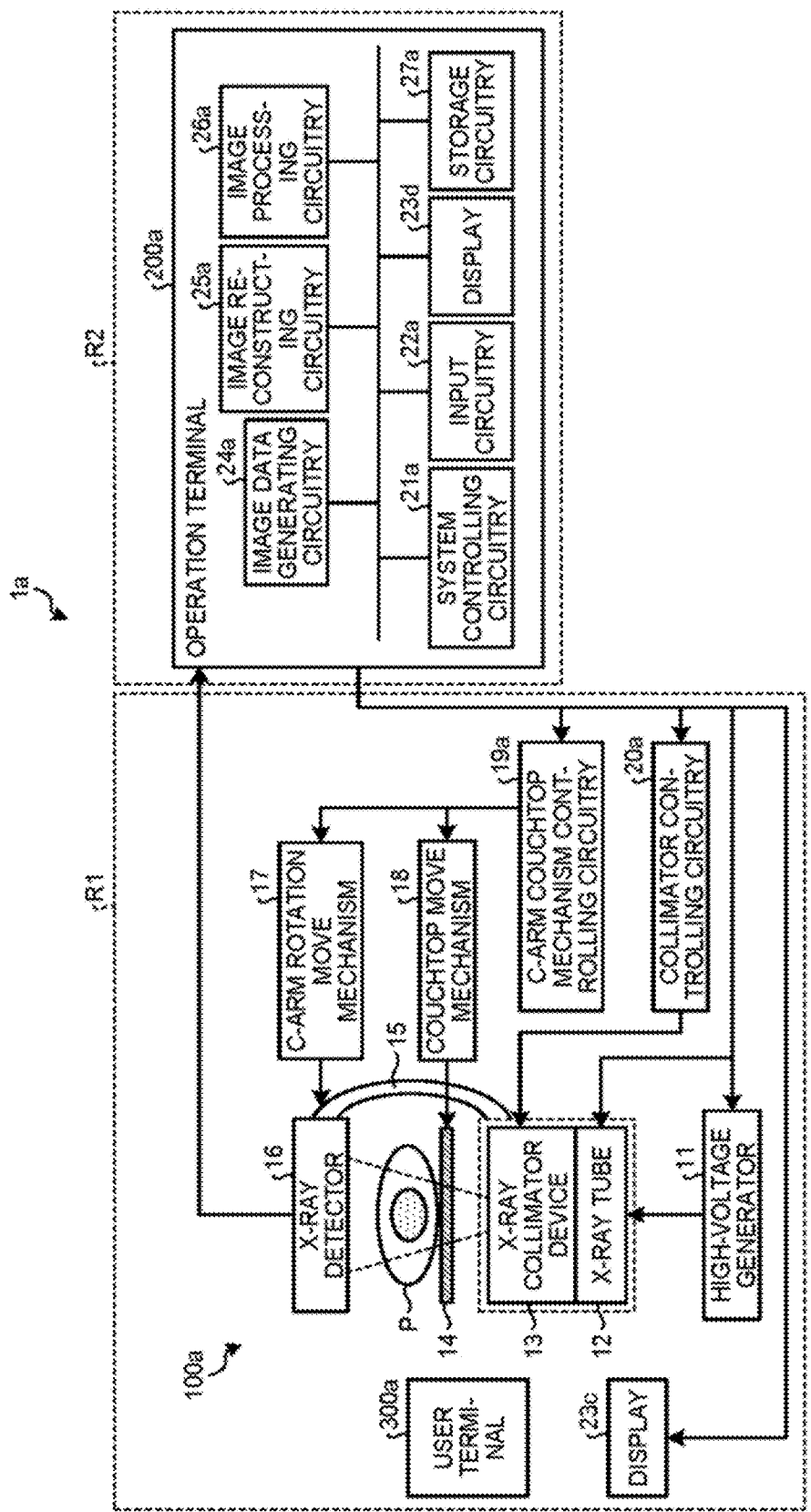
FIG. 22 is a diagram illustrating an exemplary whole configuration of an X-ray angiography apparatus according to another embodiment of the present invention.
Figure 23:
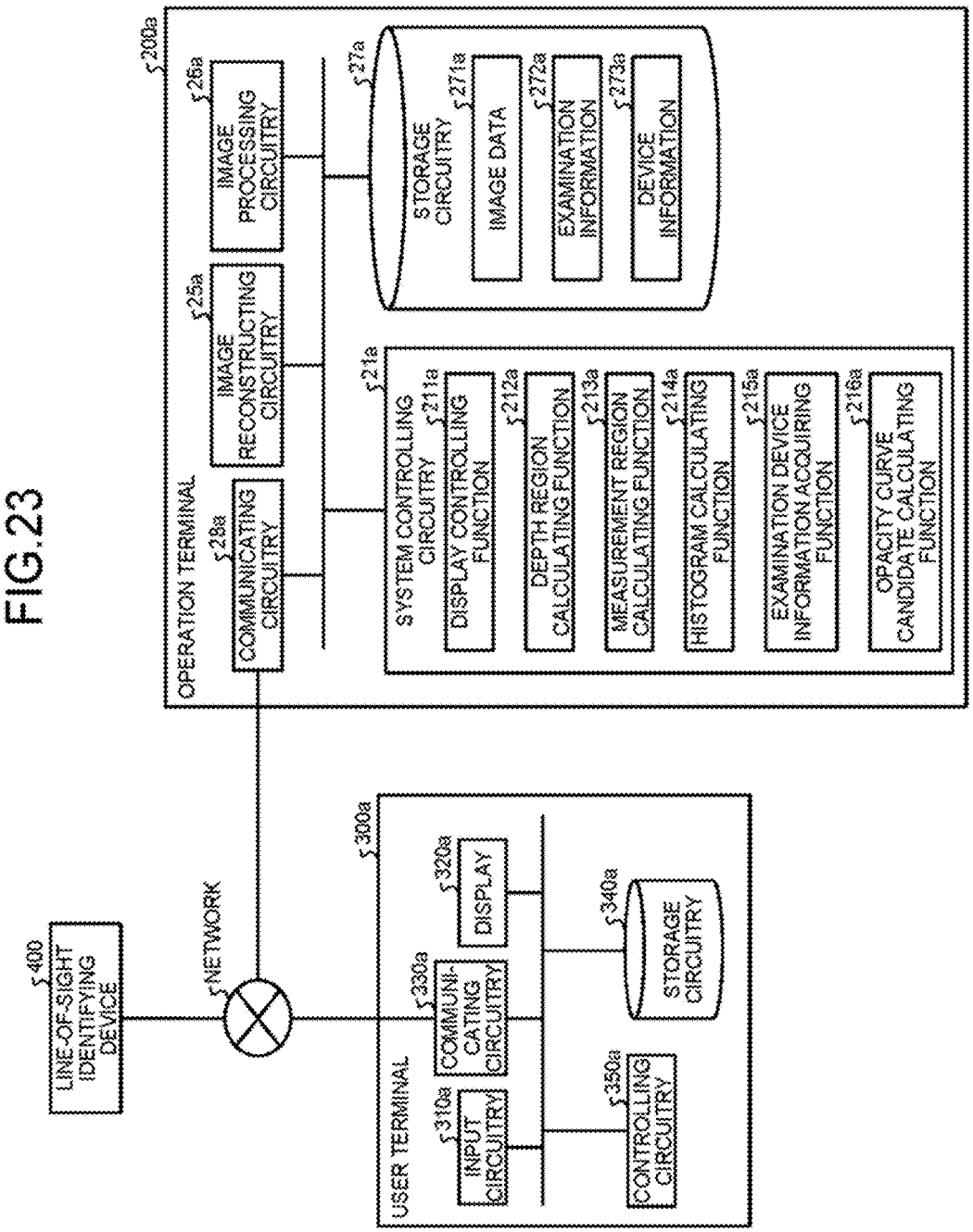
FIG. 23 is a diagram illustrating an exemplary detailed whole configuration of an X-ray angiography apparatus according to still another embodiment of the present invention.

Other embodiments of the above-described X-ray angiography apparatus will be described with reference to FIGS. 22 and 23. FIG. 22 is a diagram illustrating an exemplary whole configuration of an X-ray angiography apparatus 1*a* according to another embodiment. FIG. 23 is a diagram illustrating an exemplary detailed configuration of the X-ray angiography apparatus 1*a* according the embodiment. The operations of the components of the embodiment described below are the same as those of the first embodiment denoted by the same reference numerals, and redundant descriptions thereof will be omitted as appropriate. As shown in FIG. 22, the X-ray angiography apparatus 1*a* according to the embodiment includes an apparatus main unit 100*a* and an operation terminal 200*a*. As shown in FIG. 22, the apparatus main unit 100*a* includes the high-voltage generator 11, the X-ray tube 12, the X-ray collimator device 13, the couchtop 14, the C-arm 15, the X-ray detector 16, the C-arm rotation move mechanism 17, the couchtop move mechanism 18, C-arm couchtop mechanism controlling circuitry 19*a*, collimator controlling circuitry 20*a*, and a display 23*c*. The apparatus main unit 100*a* is disposed in the examination room R1. As shown in FIG. 22*a*, the operation terminal 200*a* includes system controlling circuitry 21*a*, input circuitry 22*a*, a display 23*d*, image data generating circuitry 24*a*, image reconstructing circuitry 25*a*, and image processing circuitry 26*a*, and storage circuitry 27*a*. The operation terminal 200*a* is disposed in the operation room R2. The operation terminal 200 communicates with a user terminal 300*a* that is disposed in the examination room R1.

The C-arm couchtop mechanism controlling circuitry 19*a* corresponds to the C-arm couchtop mechanism controller 19 shown in FIG. 3. The collimator controlling circuitry 20*a* corresponds to the collimator controller 20 shown in FIG. 3. The display 23*c* corresponds to the display unit 23*a* shown in FIG. 3. The system controlling circuitry 21*a* corresponds to the system controlling unit 21 shown in FIG. 3. The input circuitry 22*a* corresponds to the input unit 22 shown in FIG. 3. The display 23*d* corresponds to the display unit 23*b* shown in FIG. 3. The image data generating circuitry 24*a* corresponds to the image data generating unit 24 shown in FIG. 3. The image reconstructing circuitry 25*a* corresponds to the image reconstructing unit 25 shown in FIG. 3. The image processing circuitry 26*a* corresponds to the image processing unit 26 shown in FIG. 3. The storage circuitry 27*a* corresponds to the storage unit 27 shown in FIG. 3. The user terminal 300*a* corresponds to the user terminal 300 shown in FIG. 3.

Furthermore, as shown in FIG. 23, the X-ray angiography apparatus 1*a* according to the embodiment includes a communicating circuitry 28*a* corresponding to the communicating unit 28 shown in FIG. 4. As shown in FIG. 23, the various circuitry of the X-ray angiography apparatus 1*a* are connected one another and perform the same processing as that performed by the X-ray angiography apparatus 1 by transmitting and receiving various electric signals between the circuitry. Input circuitry 310*a*, a display 320*a*, communicating circuitry 330*a*, storage circuitry 340*a*, and controlling circuitry 350*a* correspond respectively to the input unit 310, the display unit 320, the communicating unit 330, the storage unit 340, and the controlling unit 350 that are shown in FIG. 4.

According to the embodiment, various processing functions implemented by the C-arm couchtop mechanism controller 19, the collimator controller 20, the system controlling unit 21, the image data generating unit 24, the image reconstructing unit 25, the image processing unit 26, and the communicating unit 28 that are shown in FIG. 3 and FIG. 4 are stored in a form of a computer-executable program in the storage circuitry 27*a*. The C-arm couchtop mechanism controlling circuitry 19*a*, the collimator controlling circuitry 20*a*, the system controlling circuitry 21*a*, the image data generating circuitry 24*a*, the image reconstructing circuitry 25*a*, the image processing circuitry 26*a*, and the communicating circuitry 28*a* are processors that implement the functions corresponding to the respective programs by executing the programs from the storage circuitry 27*a* and executing the programs. In other words, the circuitry that have loaded the respective programs have the functions corresponding to the read programs.

The word "processor" used in the descriptions herein refers to a circuit, such as a central processing unit (CPU), a graphics processing unit (GPU), an application specific integrated circuit (ASIC), or a programmable logic device (such as a simple programmable logic device (SPLD), a complex programmable logic device (CPLD), or a field programmable gate array (FPGA)). The processors implement the functions by reading the programs saved in the storage circuitry and executing the programs. Instead of saving the programs in the storage circuitry, the programs may be embedded in the circuits of the processors. In this case, the processors implement the functions by reading the programs embedded in the circuits and executing the programs. The processors of the embodiment may be configured as respective single circuits, or multiple independent circuits may be combined into a single processor, to implement the functions.

For example, the storage circuitry 27*a* stores, in addition to programs corresponding to image data 271*a*, examination information 272*a*, and device information 273*a* that are shown in FIG. 23, programs corresponding to a display controlling function 211*a*, a depth region calculating function 212*a*, a measurement region calculating function 213*a*, a histogram calculating function 214*a*, an examination device information acquiring function 215*a*, and an opacity curve candidate calculating function 216*a*. The system controlling circuitry 21*a* performs the same processing as that performed by the display controlling unit 211 by reading the program corresponding to the display controlling function 211*a* from the storage circuitry 27*a* and executing the program. The system controlling circuitry 21*a* further performs the same processing as that performed by the depth region calculating unit 212 by reading the program corresponding to the depth region calculating function 212*a* from the storage circuitry 27*a* and executing the program. The system controlling circuitry 21*a* further performs the same processing as that performed by the measurement region calculating unit 213 by reading the program corresponding to the measurement region calculating function 213*a* from the storage circuitry 27*a* and executing the program. The system controlling circuitry 21*a* further performs the same processing as that performed by the histogram calculating unit 214 by reading the program corresponding to the histogram calculating function 214*a* from the storage circuitry 27*a* and executing the program. The system controlling circuitry 21*a* further performs the same processing as that performed by the examination device information acquiring unit 215 by reading the program corresponding to the examination device information acquiring function 215*a* from the storage circuitry 27*a* and executing the program. The system controlling circuitry 21*a* further performs the same processing as that performed by the opacity curve candidate calculating unit 216 by reading the program corresponding to the opacity curve candidate calculating function 216*a* from the storage circuitry 27*a* and executing the program. Furthermore, for example, the storage circuitry 27*a* stores a program corresponding to a system controlling function for controlling the whole X-ray angiography apparatus. The system controlling circuitry 21*a* performs the same processing as that performed by the system controlling unit 21 by reading the program corresponding to the system controlling function and executing the program.

Furthermore, for example, the storage circuitry 27*a* stores programs corresponding to a C-arm couchtop mechanism controlling function, a collimator controlling function, an image data generating function, an image reconstructing function, and an image processing function. The C-arm couchtop mechanism controlling circuitry 19*a*, the collimator controlling circuitry 20*a*, the image data generating circuitry 24*a*, the image reconstructing circuitry 25*a*, and the image processing circuitry 26*a* perform the same processing as that performed by the C-arm couchtop mechanism controller 19, the collimator controller 20, the image data generating unit 24, the image reconstructing unit 25, and the image processing unit 26 by respectively reading the programs corresponding to the C-arm couchtop mechanism controlling function, the collimator controlling function, the image data generating function, the image reconstructing function, and the image processing function from the storage circuitry 27*a* and executing the programs.

FIG. 23 exemplifies the case where the single system controlling circuitry 21*a* executes each of the programs to implement the display controlling function 211*a*, the depth region calculating function 212*a*, the measurement region calculating function 213*a*, the histogram calculating function 214*a*, the examination device information acquiring function 215*a*, and the opacity curve candidate calculating function 216*a*; however, embodiments of the invention are not limited to this. For example, multiple processing circuits may implement the display controlling function 211*a*, the depth region calculating function 212*a*, the measurement region calculating function 213*a*, the histogram calculating function 214*a*, the examination device information acquiring function 215*a*, and the opacity curve candidate calculating function 216*a*. For example, one or more functions of the display controlling function 211*a*, the depth region calculating function 212*a*, the measurement region calculating function 213*a*, the histogram calculating function 214*a*, the examination device information acquiring function 215*a*, and the opacity curve candidate calculating function 216*a* may be separately implemented in one or more dedicated independent program execution circuits.

Alternatively, the circuitry shown in FIGS. 22 and 23 may be implemented as a single processing circuit. For example, one program execution circuit (processing circuit) may implement the C-arm couchtop mechanism controlling function implemented by the C-arm couchtop mechanism controlling circuitry 19*a*, the collimator controlling function implemented by the collimator controlling circuitry 20a, the image data generation function implemented by the image data generating circuitry 24a, the image reconstruction function implemented by the image reconstructing circuitry 25a, the image processing function implemented by the image processing circuitry 26a, the display controlling function 211a, the depth region calculating function 212a, the measurement region calculating function 213a, the histogram calculating function 214a, the examination device information acquiring function 215a, and the opacity curve candidate calculating function 216a that are implemented by the system controlling circuitry 21a.

The input circuitry 22a is realized by using a track ball, a switch button, a mouse, a keyboard, etc., for setting a setting region (region of attention) etc. The input circuitry 22a is connected to the system controlling circuitry 21a. The input circuitry 22a converts input operations received from the operator into electronic signals and outputs the electronic signals to the system controlling circuitry 21a.

For example, step S101 shown in FIG. 19 is the step implemented by the system controlling circuitry 21a by reading the program corresponding to the display controlling function 211a from the storage circuitry 27a and executing the program. Step S102 and step S103 shown in FIG. 19 are the steps implemented by the system controlling circuitry 21a by reading the program corresponding to the depth region calculating function 212a from the storage circuitry 27a and executing the program. Step S104 shown in FIG. 19 is the step implemented by the system controlling circuitry 21a by reading the program corresponding to the measurement region calculating function 213a from the storage circuitry 27a and executing the program. Step S105 shown in FIG. 19 is the step implemented by the system controlling circuitry 21a by reading the program corresponding to the histogram calculating function 214a from the storage circuitry 27a and executing the program. Step S106 shown in FIG. 19 is the step implemented by the system controlling circuitry 21a by reading the program corresponding to the examination device information acquiring function 215a from the storage circuitry 27a and executing the program. Step S107 shown in FIG. 19 is the step implemented by the system controlling circuitry 21a by reading the program corresponding to the opacity curve candidate calculating function 216a from the storage circuitry 27a and executing the program. Step S108 shown in FIG. 19 is the step implemented by the image reconstructing circuitry 25a by reading the program corresponding to the image reconstruction function from the storage circuitry 27a and executing the program. Step S109 shown in FIG. 19 is the step implemented by the image reconstructing circuitry 25a by reading the program corresponding to the image reconstruction function from the storage circuitry 27a and executing the program.

For example, the processing shown in FIG. 20 is the processing implemented by the system controlling circuitry 21a by reading the program corresponding to the measurement region calculating function 213a from the storage circuitry 27a and executing the program. For example, the processing shown in FIG. 21 is the processing implemented by the system controlling circuitry 21a by reading a program corresponding to a system function from the storage circuitry 27a and executing the program.

As described above, according to the first and second embodiments, the X-ray angiography apparatuses according to the first and second embodiments makes it easy to make an easy-to-see display of a site to be measured.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnostic apparatus comprising:
   storage circuitry configured to store three-dimensional medical image data that is obtained by imaging a subject; and
   processing circuitry configured to
      set a first region of attention in a first medical image in which the subject is shown from a first direction in the three-dimensional medical image data and a second region of attention in a second medical image in which the subject is shown from a second direction different from the first direction in the three-dimensional medical image data, based on operations accepted from an operator or the operator's line of sight with respect to the first medical image and the second medical image,
      calculate a first depth region that is three-dimensional region obtained by extending the first region of attention in the depth direction on the three-dimensional medical image data and a second depth region that is three-dimensional region obtained by extending the second region of attention in the depth direction on the three-dimensional medical image data,
      calculate, as the region of interest, a group of voxels contained in both the first depth region and the second depth region,
      determine, based on voxel values of the region of interest, a candidate for parameter value relating to image processing on a medical image to be generated from the three-dimensional medical image data, and
      cause a display to display the candidate for parameter value.

2. The medical image diagnostic apparatus according to claim 1, wherein
   the processing circuitry is configured to determine a plurality of candidates for parameter values,
   the processing circuitry is configured to
      further generate a plurality of candidate images corresponding to the plurality of candidates for parameter value, respectively, and
      cause the display to display the plurality of candidates for the parameter values and the plurality of candidate images.

3. The medical image diagnostic apparatus according to claim 1, wherein the first medical image and the second medical image are images before reconstruction that are used to reconstruct the three-dimensional medical image data.

4. The medical image diagnostic apparatus according to claim 1, wherein the processing circuitry is configured to determine the candidate for the parameter value by using a histogram of the voxel values of the region of interest.

5. The medical image diagnostic apparatus according to claim 4, wherein the processing circuitry is configured to determine, as candidate for parameter value, a range for which opacity is varied in the histogram of the voxel values of the region of interest and a pattern for varying the opacity in the range.

6. The medical image diagnostic apparatus according to claim 5, wherein the processing circuitry is configured to determine, as the range for which the opacity is varied, a range where a threshold of frequency that is set based on the type of the region of interest in the histogram of the voxel values of the region of interest is exceeded.

7. The medical image diagnostic apparatus according to claim 5, wherein the processing circuitry is configured to determine a band of voxel values corresponding to the type of the region of interest as the range for which the opacity is varied.

8. The medical image diagnostic apparatus according to claim 5, wherein the processing circuitry is configured to determine a range to be excluded from a range for which the parameter is set by using the histogram of the voxel values of the three-dimensional medical image data.

9. The medical image diagnostic apparatus according to claim 1, wherein
the processing circuitry is configured to
accept a setting for the first region of attention in the first medical image and a setting for the second region of attention in the second medical image, and
calculate the region of interest in the three-dimensional medical image data on the basis of the accepted first region of attention and the accepted second region of attention.

10. The medical image diagnostic apparatus according to claim 9,
wherein the processing circuitry is configured to
accept, as the first region of attention, a region gazed by an operator in the first medical image, and
accept, as the second region of attention, a region gazed by an operator in the second medical image.

11. The medical image diagnostic apparatus according to claim 9,
wherein the processing circuitry is configured to
accept, as the first region of attention, a region set by the operator in the first medical image, and
accept, as the second region of attention, a region set by the operator in the second medical image.

12. The medical image diagnostic apparatus according to claim 9, wherein
the processing circuitry is configured to
accept, as the first region of attention and the second region of attention, at least any one of regions gazed by an operator during radiography using an X-ray and regions on which spot radiography is performed, and
calculate, on the basis of the accepted first region of attention and the accepted second region of attention, the region of interest in the three-dimensional medical image data on the subject that is imaged by using the x-ray.

* * * * *